US012408838B2

(12) United States Patent
Tang et al.

(10) Patent No.: US 12,408,838 B2
(45) Date of Patent: Sep. 9, 2025

(54) APPARATUS AND METHOD FOR TOOTH PULP VITALITY DETECTION

(71) Applicants: UNIVERSITY OF MARYLAND, BALTIMORE, Baltimore, MD (US); THE UNITED STATES GOVERNMENT AS REPRESENTED BY THE DEPARTMENT OF VETERANS AFFAIRS, Washington, DC (US)

(72) Inventors: Cha-Min Tang, Wayne, PA (US); Joseph Schmitt, Cupertino, CA (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 47 days.

(21) Appl. No.: 18/304,711

(22) Filed: Apr. 21, 2023

(65) Prior Publication Data

US 2023/0263398 A1 Aug. 24, 2023

Related U.S. Application Data

(63) Continuation of application No. 16/487,775, filed as application No. PCT/US2018/019164 on Feb. 22, 2018, now Pat. No. 11,666,223.

(Continued)

(51) Int. Cl.
*A61B 5/00* (2006.01)
*A61B 5/026* (2006.01)
(Continued)

(52) U.S. Cl.
CPC .......... *A61B 5/0088* (2013.01); *A61B 5/0066* (2013.01); *A61B 5/0261* (2013.01); (Continued)

(58) Field of Classification Search
CPC ... A61B 5/0088; A61B 5/0066; A61B 5/0261; A61B 5/4547; A61B 5/682;
(Continued)

(56) References Cited

U.S. PATENT DOCUMENTS 5,259,761 A * 11/1993 Schnettler .............. A61C 19/04
600/323
5,584,596 A 12/1996 Greene
(Continued)

FOREIGN PATENT DOCUMENTS

DE 19649689 A1 * 6/1998 .......... A61B 5/0088
EP 3228241 A1 10/2017
WO 2007/072592 A1 6/2007

OTHER PUBLICATIONS

Fein, Michael E., et al. "Evaluation of optical methods of detecting dental pulp vitality." Journal of Biomedical Optics 2.1 (1997): 58-73. (Year: 1997).*
(Continued)

*Primary Examiner* — Sean D Mattson
(74) *Attorney, Agent, or Firm* — Wolter Van Dyke Davis, PLLC; Eugene J. Molinelli; Cian G. O'Brien

(57) ABSTRACT

An apparatus provided for detecting tooth pulp vitality includes a handle, a pivot and a caliper. A pair of fiber optic lines pass through an interior of the handle, the pivot and the caliper. One of the fiber optic lines is a source line with a connector at an end of the source line and another of the fiber optic lines is a detector line with a connector at an end of the detector line. The source line is single mode in the handle and the detector line is multi mode. A system is also provided for detecting tooth pulp vitality that includes the apparatus. Additionally, a method is provided for detecting tooth pulp vitality that employs the apparatus.

20 Claims, 18 Drawing Sheets

Related U.S. Application Data

(60) Provisional application No. 62/582,518, filed on Nov. 7, 2017, provisional application No. 62/461,955, filed on Feb. 22, 2017.

(51) Int. Cl.
  *A61B 90/00* (2016.01)
  *A61C 3/10* (2006.01)
  *A61C 19/04* (2006.01)

(52) U.S. Cl.
  CPC ............ *A61B 5/4547* (2013.01); *A61B 5/682* (2013.01); *A61B 90/361* (2016.02); *A61B 2090/3614* (2016.02); *A61C 3/10* (2013.01); *A61C 19/04* (2013.01)

(58) Field of Classification Search
  CPC .......... A61B 5/6887; A61B 2090/3614; A61B 2505/05; A61C 3/10; A61C 19/04
  See application file for complete search history.

(56) References Cited

U.S. PATENT DOCUMENTS

| | | | |
|---|---|---|---|
| 6,445,939 B1* | 9/2002 | Swanson | A61B 5/0066 385/33 |
| 6,485,413 B1* | 11/2002 | Boppart | G01N 21/4795 600/478 |
| 11,666,223 B2* | 6/2023 | Tang | A61B 5/0066 433/29 |
| 2001/0055462 A1* | 12/2001 | Seibel | A61B 1/00048 385/33 |
| 2006/0132790 A1* | 6/2006 | Gutin | G01B 9/02034 356/479 |
| 2007/0268456 A1* | 11/2007 | Ohbayshi | A61B 5/0073 351/246 |
| 2008/0291463 A1* | 11/2008 | Milner | G01B 9/02069 356/491 |
| 2012/0243251 A1* | 9/2012 | Suzuki | A61B 1/055 29/428 |
| 2014/0043618 A1* | 2/2014 | Tang | A61B 5/7415 356/402 |
| 2014/0150272 A1 | 6/2014 | Emtman et al. | |
| 2018/0296098 A1 | 10/2018 | Islam | |
| 2019/0110689 A1 | 4/2019 | Ertl et al. | |
| 2021/0369120 A1* | 12/2021 | Ertl | A61B 5/682 |

OTHER PUBLICATIONS

Ahmad et al., Sonification of optical coherence tomography data and images, Opt. Express, 2010, pp. 9934-9944, vol. 18.

Binder et al., Hemorrhagic complications of microelectrode-guided deep brain stimulation, Stereotactic and Functional Neurosurgery, 2003, pp. 28-31, vol. 80.

Chen et al., Noninvasive imaging of in vivo blood flow velocity using optical Doppler tomography, Optics Letters, 1997, pp. 1119-1121, vol. 22.

Eun, Evaluation of skin blood flow by laser Doppler flowmetry, Clin Dermatol, 1995, pp. 337-347, vol. 13.

Fredriksson et al., Laser Doppler Flowmetry—A Theoretical Framework, Department of Biomedical Engineering, Linköping University, 2007, pp. 1-22.

Gazelius et al., Laser Doppler flowmetry in assessing vitality in luxated permanent teeth, International Endodontic Journal, 1988, pp. 300-306, vol. 21.

Gazelius et al., Restored vitality in luxated teeth assessed by laser Doppler flowmeter, Endodontics & Dental Traumatology, 1988, pp. 265-268, vol. 4.

International Search Report and Written Opinion of the International Searching Authority, issued in connection with Int'l Appl. No. PCT/US18/19164, dated May 4, 2018 (6 pages).

Jones et al., Near-infrared transillumination at 1310-nm for the imaging of early dental decay, Optics Express, 2003, pp. 2259-2265, vol. 11.

Kijsamanmith et al., Pulpal blood flow recorded from human premolar teeth with a laser Doppler flow meter using either red or infrared light, Arch Oral Biol, 2011, pp. 629-633, vol. 56.

Petersson et al., Evaluation of the ability of thermal and electrical tests to register pulp vitality, Endodontics & Dental Traumatology, 1999, pp. 127-131, vol. 15.

Podoleanu, Unbalanced versus balanced operation in an optical coherence tomography system, Applied Optics, 2000 pp. 173-182, vol. 39.

Pozzobon et al., Assessment of pulp blood flow in primary and permanent teeth using pulse oximetry, Dental Traumatology, 2011, pp. 184-188, vol. 27.

Schmitt et al., Optical determination of dental pulp vitality, IEEE Transactions on Biomedical Engineering, 1991, pp. 346-352, vol. 38.

Soo-Ampon et al., The sources of laser Doppler blood-flow signals recorded from human teeth, Archives of Oral Biology, 2003, pp. 353-360, vol. 48.

Varghese et al., Path-length-resolved measurements of multiple scattered photons in static and dynamic turbid media using phasemodulated low-coherence interferometry, Journal of Biomedical Optics, 2007, pp. 024020, vol. 12.

Wardell et al., Intracerebral microvascular measurements during deep brain stimulation implantation using laser Doppler perfusion monitoring, Stereotactic and Functional Neurosurgery, 2007, pp. 279-286, vol. 85.

Weisleder et al., The validity of pulp testing: a clinical study, Journal of the American Dental Association, 2009, pp. 1013-1017, vol. 140.

Yang et al., High speed, wide velocity dynamic range Doppler optical coherence tomography (Part I): System design, signal processing, and performance, Opt Express, 2003, pp. 794-809, vol. 11.

Marc F. Swiontkowski, et al.; "Laser Doppler Flowmetry—Development and Clinical Application," Iowa Orthopaedic Journal, v11, pp. 119-126 (1991).

* cited by examiner

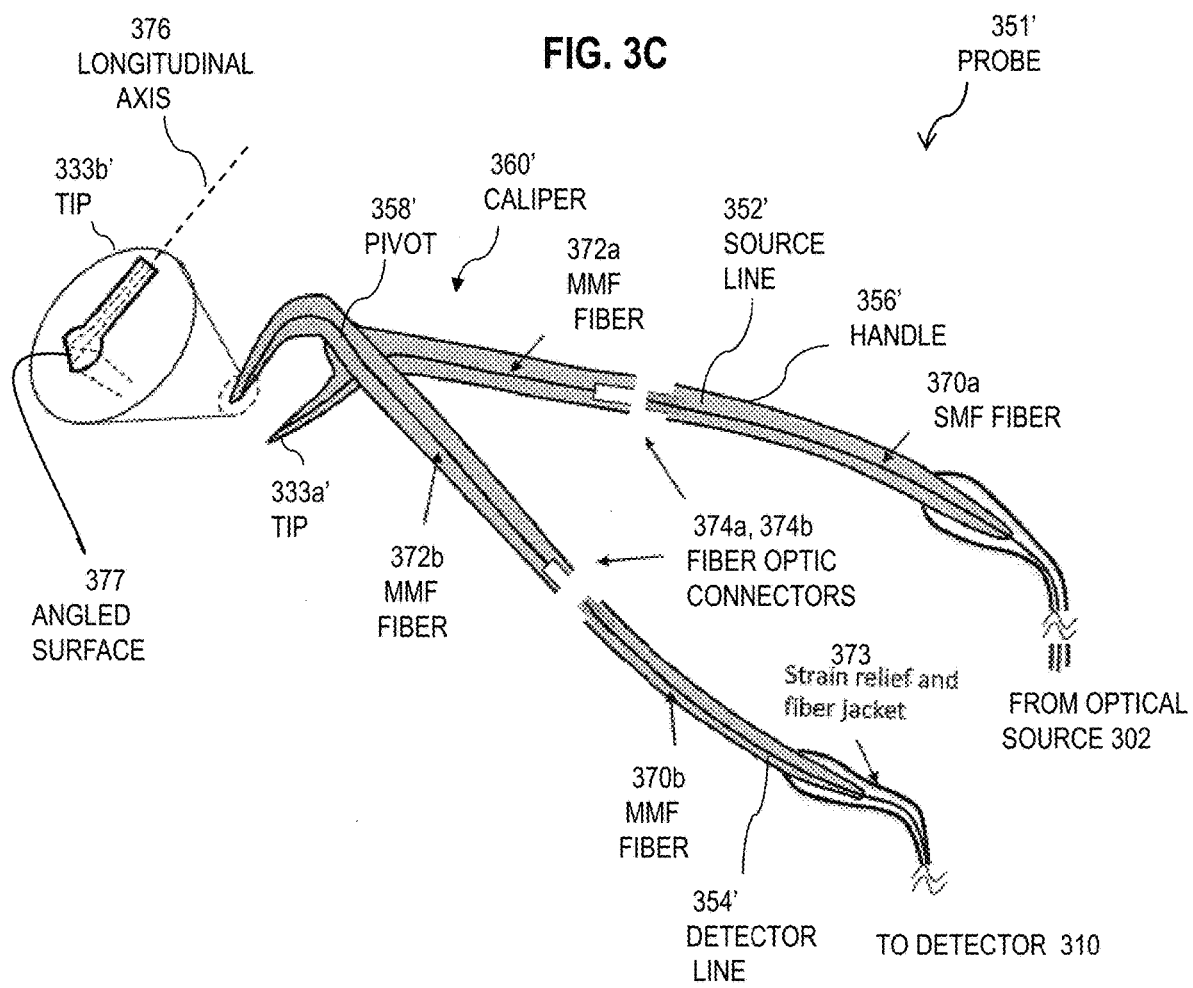

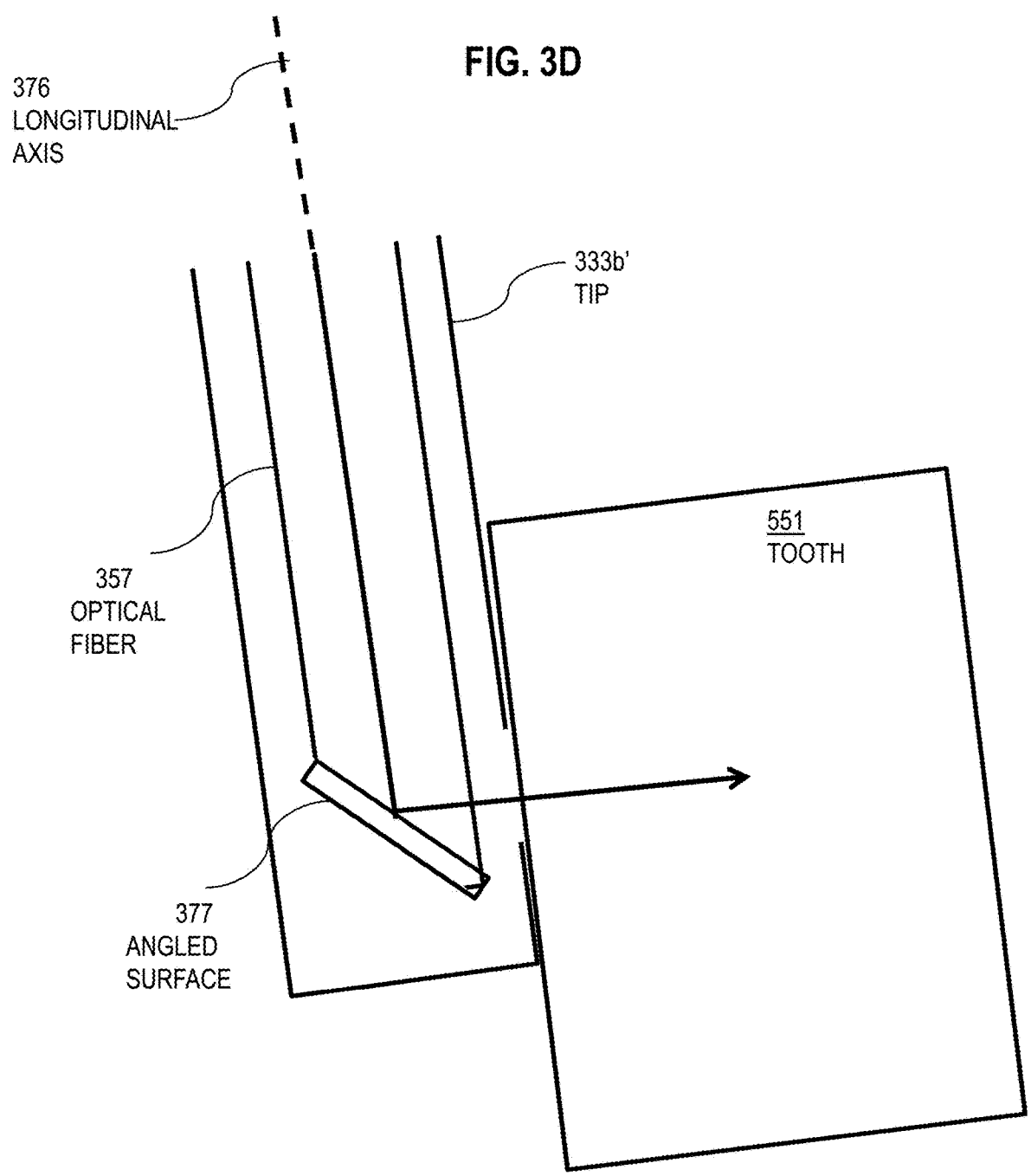

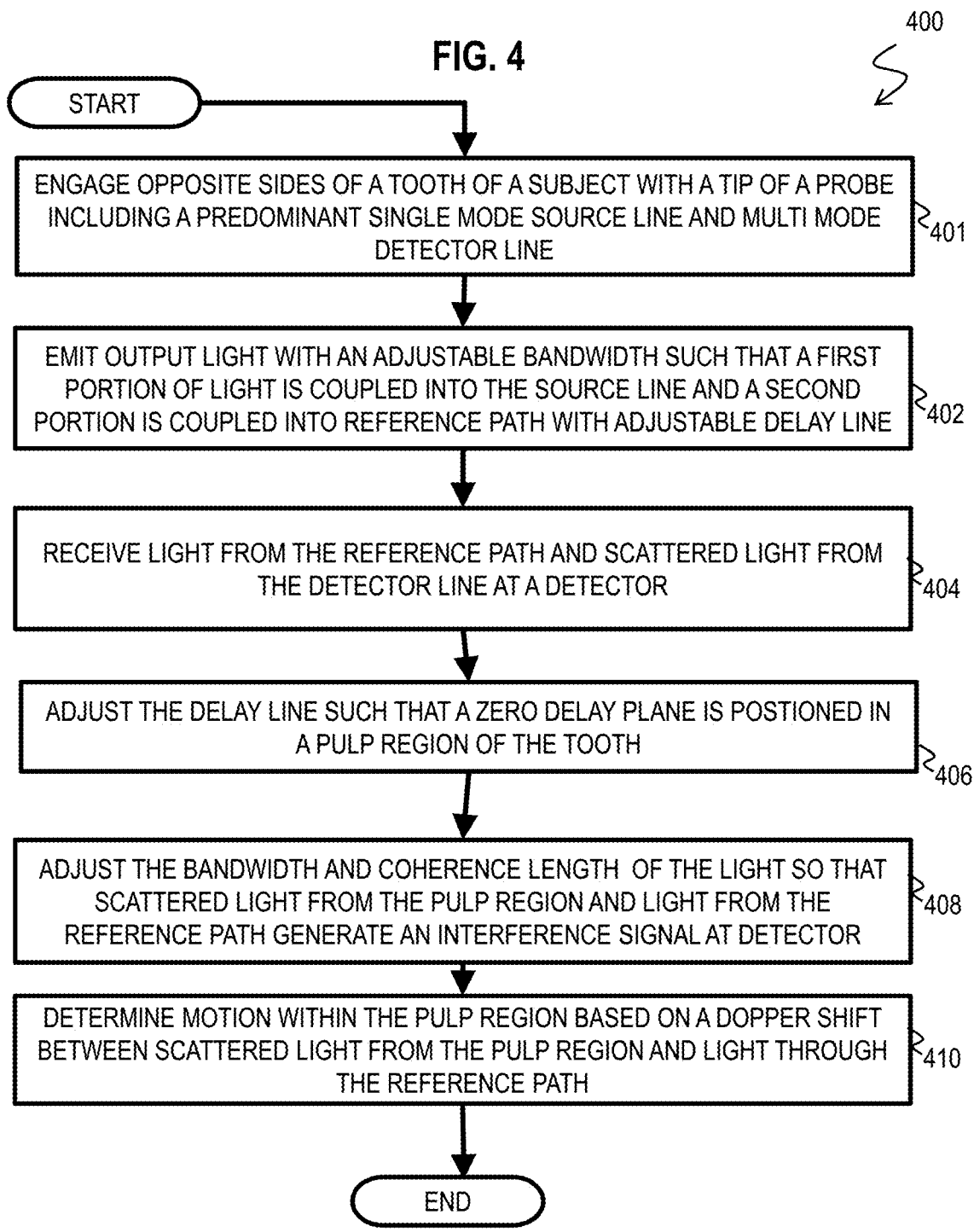

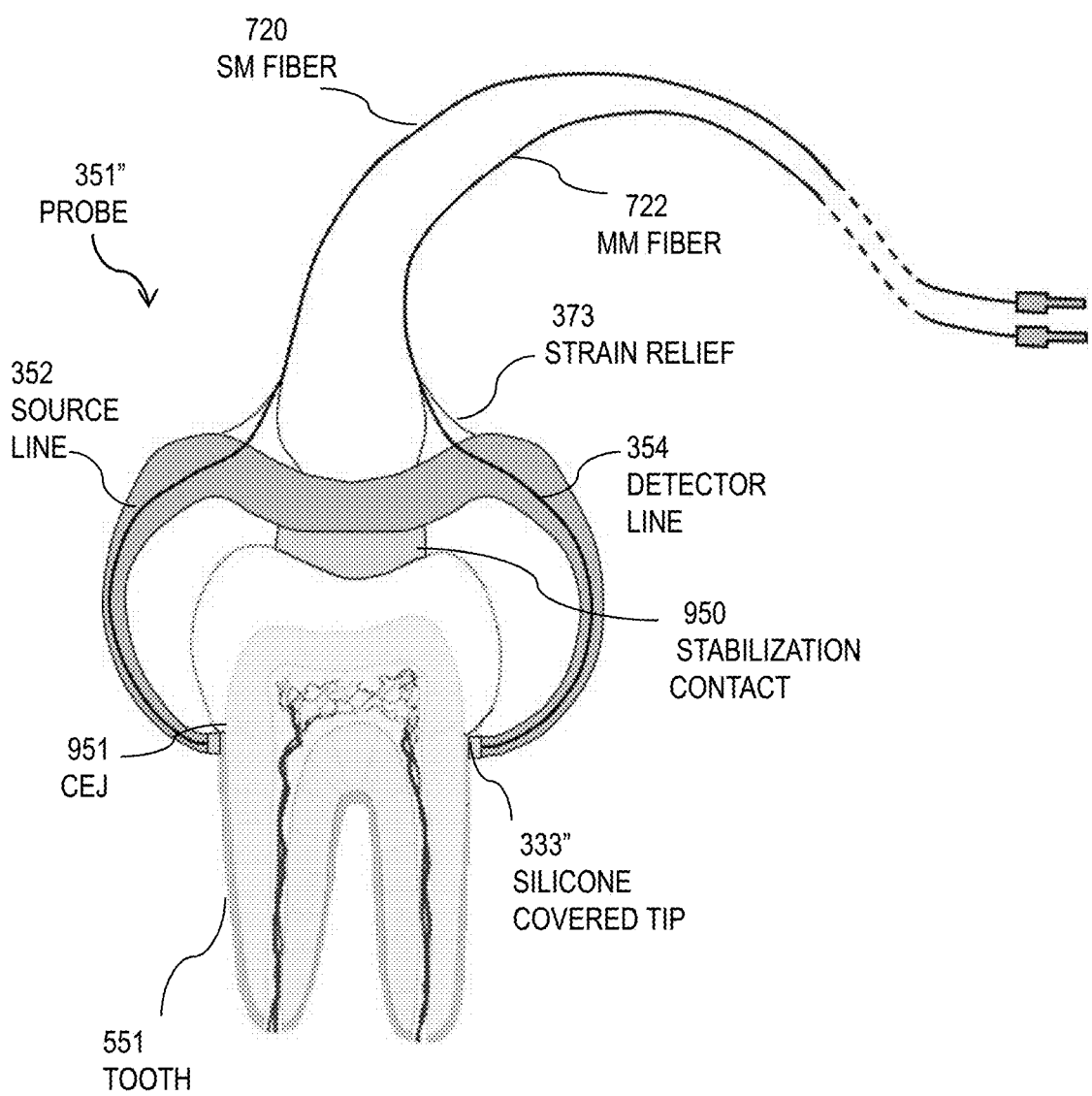

APPARATUS AND METHOD FOR TOOTH PULP VITALITY DETECTION

CROSS-REFERENCE TO RELATED APPLICATIONS

This application is continuation of U.S. patent application Ser. No. 16/487,775, filed Aug. 21, 2019, which is a 371 National Stage Application of PCT Application No. PCT/US18/19164, filed Feb. 22, 2018, and claims benefit of Provisional Application No. 62/461,955, filed Feb. 22, 2017, the entire contents of which are hereby incorporated by reference as if fully set forth herein, under 35 U.S.C. § 119(e). This application also claims benefit of Provisional Application No. 62/582,518, filed Nov. 7, 2017, the entire contents of which are hereby incorporated by reference as if fully set forth herein, under 35 U.S.C. § 119(e).

BACKGROUND

Motion sensors have a wide range of applications and are implemented using a wide range of techniques exploiting a wide range of physical principles. Medical applications for motion sensors include diagnosis and treatment of a subject based on the presence, function or location of blood vessels that carry moving blood cells and other constituents. Sometimes the tissue, such as bone, is difficult to penetrate for obtaining the motion measurement. Only a few motion sensors are suitable for such varied medical applications.

One technique that has been used in medical applications is laser Doppler flowmetry (LDF). As stated in Marc F. Swiontkowski, "Laser Doppler Flowmetry—Development and Clinical Application," *Iowa Orthopaedic Journal*, v11, pp119-126 (1991), "Laser Doppler Flowmetry (LDF) is an accurate and reliable method for assessing microcirculatory function. Through a series of in vitro and in vivo experiments, LDF output has been shown to be reproducible and to correlate with bone blood flow as estimated by other methods. The utility of the method in assessing meniscal, tendonous, and ligamentous perfusion has also been demonstrated. LDF has proven potential in clinical research in osteonecrosis, osteomyelitis, fracture healing, and other areas." LDF has also been applied to neurosurgery, dermatology and dentistry. However, these devices suffer from low signal to noise ratio and low spatial resolution compared to blood vessels of interest during many diagnosis and treatment procedures.

Another technique used in medical applications is Doppler optical coherence tomography (DOCT). Optical coherence tomography (OCT) is an optical signal acquisition and processing method. It captures micrometer-resolution, three-dimensional images from within optical scattering media (e.g., biological tissue). Depending on the properties of the light source (superluminescent diodes, ultrashort pulsed lasers and supercontinuum lasers have been employed), optical coherence tomography has achieved sub-micrometer resolution (with very wide-spectrum sources emitting over a range of wavelengths about 100 nanometers wide, 1 nanometer, nm, $=10^{-9}$ meters). Commercially available optical coherence tomography systems are employed in diverse applications, including diagnostic medicine, notably in ophthalmology where it can be used to obtain detailed images from within the retina. Recently it has also begun to be used in interventional cardiology to help diagnose coronary artery disease. Determining the Doppler shift in the returned signal due to motion of the optical scatterers in the sample, turns the OCT into a 3D imaging DOCT motion sensor. However, these devices are expensive, complicated, unwieldy and difficult to use when diagnosing or treating patients.

Yet another technique used in medical applications is Coherence Gated Doppler (CGD) Motion Sensing. CGD involves adjusting a bandwidth and corresponding coherence length of an optical source for purposes of capturing Doppler shifted signals from a target volume to measure motion within the target volume.

Testing the vitality of the tooth is a common procedure in dentistry when evaluating the need for a root canal procedure as a consequence of tooth decay, infection or trauma. Most available testing methods rely on subjective assessment of the sensitivity of the tooth to cold, heat, or electrical stimulation. Many dentists use a simple pulp vitality test based on application of ice or heated rubber to the tooth. To improve repeatability, others use specialized instruments that generate a localized source of heat or cold that can be applied to the tooth at a controlled temperature. Since the first invention disclosures in the early 1940's, numerous methods for electrical stimulation of the tooth have been developed, which have led to the variety of electrical pulp stimulators available in the market today. These existing methods have a sensitivity and specificity in the 80% to 90% range.

SUMMARY

Techniques are provided for simple, inexpensive, reliable, easily-used motion sensors with sufficiently high sensitivity to detect tooth pulp flow and sufficiently high specificity to distinguish it from the blood flow arising from the surrounding gum tissue and the periodontal ligament. It is here recognized that current LDF techniques are inadequate for reliable tooth pulp vitality detection. In one example, current LDF techniques feature inadequate sensitivity to pulp flow, particularly in large molars. Specifically, current LDF techniques do not account for variance in tooth thickness when measuring pulp flow. In another example, current LDF techniques are susceptible to blood flow arising outside of the tooth. Specifically, current LDF techniques are unable to isolate scattered signals from the pulp region while excluding scattered signals from tissue that immediately surrounds the tooth (e.g. gum tissue and periodontal ligament). In yet another example, current LDF techniques do not permit the use of low-cost, reusable probes that are particularly advantageous when performing tooth pulp vitality detection in multiple individuals. Specifically, current LDF techniques employ single mode fibers which require complex single mode to single mode coupling for a detachable and reusable probe tip. The system and method for tooth pulp vitality detection described herein overcomes one or more of these noted drawbacks of current LDF techniques.

In a first set of embodiments, an apparatus for detecting tooth pulp vitality includes a handle, a pivot and a caliper. A pair of fiber optic lines pass through an interior of the handle, the pivot and the caliper. One of the fiber optic lines is a source line with a connector at an end of the source line and another of the fiber optic lines is a detector line with a connector at an end of the detector line. The source line is single mode in the handle and the detector line is multi mode.

In a second set of embodiments, a system for detecting tooth pulp vitality includes a probe with a tip configured to engage opposite sides of a subject. The probe includes a pair of fiber optic lines passing through an interior of the probe. The fiber optic lines include a source line that is predominantly single mode and includes a connector at one end and a detector line that is multi mode and includes a connector at one end. The system also includes an optical source to emit output light with an adjustable bandwidth, where the optical source is coupled to the source line connector to transmit the output light into the source line. The system also includes a reference path with an adjustable delay line coupled to the optical source to receive the output light from the optical source. The system also includes a detector coupled to the adjustable delay line to receive the output light from the reference path and also coupled to the detector line connector to receive scattered light. The system also includes a processor and a memory with one or more sequence of instructions. The memory and the sequence of instructions, with the processor, are configured to cause the system to adjust the adjustable delay line of the reference path such that a zero delay plane is positioned in a target volume of the subject, where the zero delay plane is defined such that an optical path of output light through the reference path to the detector is equal to an optical path of scattered light from the zero delay plane through the detector line to the detector. The memory and sequence of instructions, along with the processor, are further configured to cause the system to adjust the bandwidth of the output light to vary a coherence length of the output light such that scattered light from the target volume and output light through the reference path generate an interference signal at the detector and such that scattered light from outside the target volume and output light through the reference path do not generate an interference signal at the detector. The memory and sequence of instructions, along with the processor, are further configured to cause the system to determine motion within the target volume based on a Doppler shift between scattered light from the target volume and the output light through the reference path, wherein the Doppler shift is based on the generated interference signal.

In a third set of embodiments, a method for detecting tooth pulp vitality includes engaging opposite sides of a tooth of a subject with a tip of a probe, where the probe includes a pair of fiber optic lines passing through an interior of the probe. The fiber optic lines include a source line that is predominantly single mode and includes a connector at one end and a detector line that is multi mode and includes a connector at one end. The method further includes emitting output light from an optical source with an adjustable bandwidth, where a first portion of the output light is coupled into the source line connector and a second portion of the output light is coupled into a reference path with an adjustable delay line. The method further includes receiving, at a detector, output light from the reference path and scattered light from the detector line connector. The method further includes adjusting the delay line of the reference path with a processor such that aa zero delay plane is positioned in the pulp region of the tooth, where the zero delay plane is defined such that an optical path of output light through the reference path to the detector is equal to an optical path of scattered light from the zero delay plane through the detector line to the detector. The method further includes adjusting the bandwidth of the output light with the processor to vary a coherence length of the output light such that scattered light from the pulp region and output light through the reference path generate an interference signal at the detector and such that scattered light from gum tissue and output light through the reference path do not generate an interference signal at the detector. The method further includes determining motion within the pulp region with the processor based on a Doppler shift between scattered light from the pulp region and output light through the reference path, where the Doppler shift is based on the generated interference signal.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 3C is a block diagram that illustrates example components of an apparatus used in the system of FIG. 3A, according to various embodiments;

FIG. 3D is a block diagram that illustrates example source line of the apparatus of FIG. 3C, according to various embodiments;

FIG. 4 is a flowchart that illustrates an example of a method for detecting tooth pulp vitality, according to various embodiments;

FIG. 9A is a block diagram that illustrates an example of positioning of a tip of the probe on opposite sides of a tooth in the system of FIG. 7, according to various embodiments;

DETAILED DESCRIPTION

A method and apparatus are described for tooth pulp vitality detection. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5x to 2x, for example, about 100 implies a value in a range from 50 to 200. Moreover, all ranges disclosed herein are to be understood to encompass any and all sub-ranges subsumed therein. For example, a range of "less than 10" for a positive parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of tooth pulp vitality detection. However, the invention is not limited to this context. In other embodiments, the invention can be employed in the detection of blood vessels in open surgical and laproroscopy procedures or localization of blood vessels in the brain during electrode insertion.

Figure 1A:
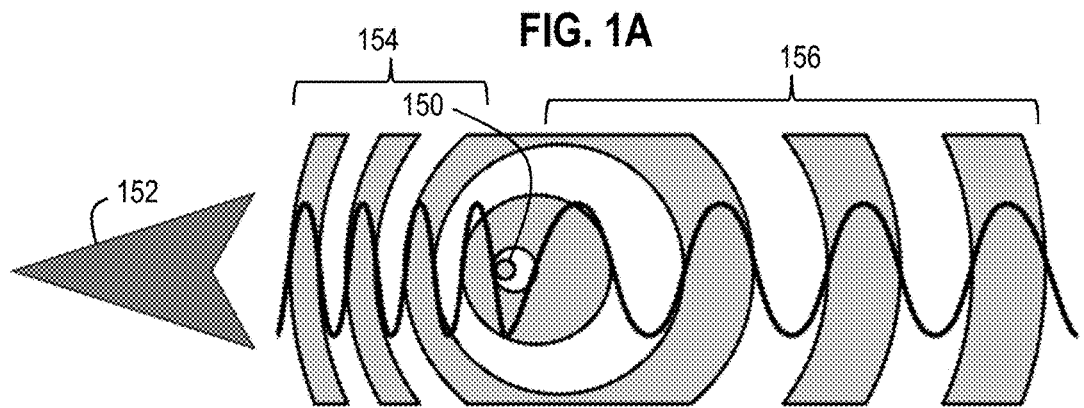
FIG. 1A through FIG. 1C are block diagrams that illustrate an example method to produce an interference signal at a detector, which indicates motion in a target volume.
Figure 1B:
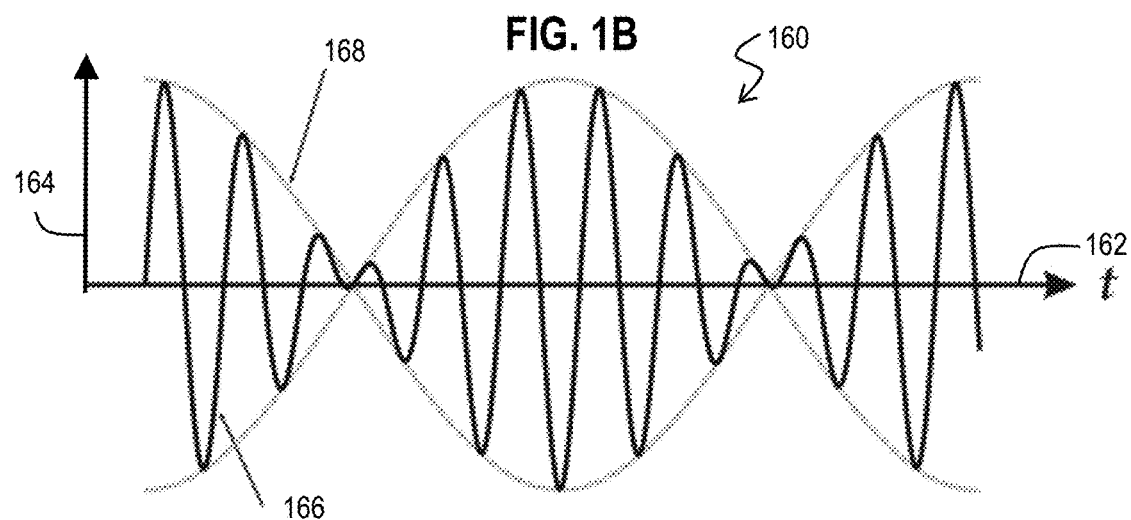
Figure 1C:
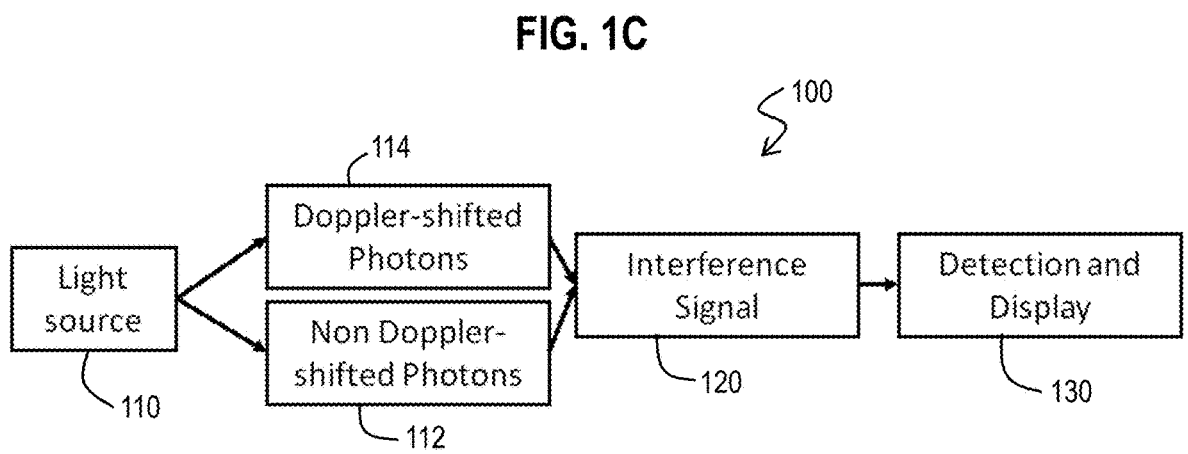

FIG. 1A through FIG. 1C are block diagrams that illustrate an example method to produce an interference signal at a detector, which indicates motion in a target volume. FIG. 1A is a block diagram that illustrates a Doppler shift in frequency and wavelength. A source 150, such as an emitter or scatterer of a wave, such as an electromagnetic wave, including light, is moving in direction 152 relative to an observer. The waves 154 propagating in the direction of movement have an increased frequency and reduced wavelength compared to that emitted or scattered from a stationary source. Similarly, the waves 156 propagating in the direction opposite to the movement have a decreased frequency and increased wavelength compared to that emitted or scattered from a stationary source. This shift in frequency and wavelength is the called a Doppler shift and is proportional to the speed v of the source 150 relative to the observer. For light waves traveling at the speed of light in the medium, given by cN where c is the speed of light in a vacuum and N is the index of refraction of the medium, the Doppler shift $\Delta\lambda$ in original wavelength $\lambda_0$ is given by Equation 1a and frequency shift by Equation 1b for an approaching source 150.

$$\Delta\lambda = -(v/cN)\lambda_0 \quad (1a)$$

$$\Delta f = (v/cN)f_0 \quad (1b)$$

The optical wavelengths are very small, occurring in a range of hundreds of nanometers (nm, 1 nm=$10^{-9}$ meters) and the corresponding frequencies are high on the order of hundreds of terahertz (THz, 1 THz=$10^{12}$ Hertz).

For many applications, such as medical applications with blood flow on the order of a meter per second, the speed v is a tiny fraction of the speed of light in the medium and so the Doppler shift is exceedingly small, on the order of $10^{-8}$ of the wavelength $\lambda$ or frequency f. Such a change is difficult to measure directly. However, if the Doppler shifted wave interacts with a non-Doppler shifted wave, the interference pattern produces a signal related to the difference between the two waves that is much easier to measure. For example, a speed on the order of 1 meter per second (m/s) for a wavelength of about 1000 nm (f of about 300 THz) has a frequency shift of about 1 MegaHertz (MHz, 1 MHz=$10^6$ Hertz, 1 Hertz, Hz, =1 cycle per second). FIG. 1B is a graph 160 that illustrates an example interference signal between two different waves. The horizontal axis 162 is time in arbitrary units, and the vertical axis 164 is amplitude in arbitrary units. The interference signal is given by trace 166, which is enclosed by an envelope 168 of much lower frequency. Even for interfering optical waves with a frequency shift of one millionth of the optical frequencies, the interference signal envelope 168 has frequency on the order of MegaHertz. For flows of about a millimeters per second, the frequency is on the order of tens of kilohertz (kHz, 1 KHZ=$10^3$ Hertz).

FIG. 1C is a block diagram that illustrates an example motion sensor system 100 based on optical measurements, as employed by many current motion sensor systems. A light source block 110 emits light of which one portion interacts with moving scatterers in block 114 and is Doppler shifted, and another portion is not Doppler shifted in block 112, either because of interaction with stationary scatterers, or because this portion propagates in a reference path free from any scatterers, or some combination. The two paths are brought together to create an interference signal in block 120, which is detected and displayed in block 130. How the different blocks are implemented varies widely in different devices. These types of existing motion sensor devices are described next: a laser Doppler flowmetry (LDE) device; a Doppler optical coherence tomography (DOCT) device; and a Coherence Gated Doppler Motion Sensing (CGD) system.

Figure 2A:
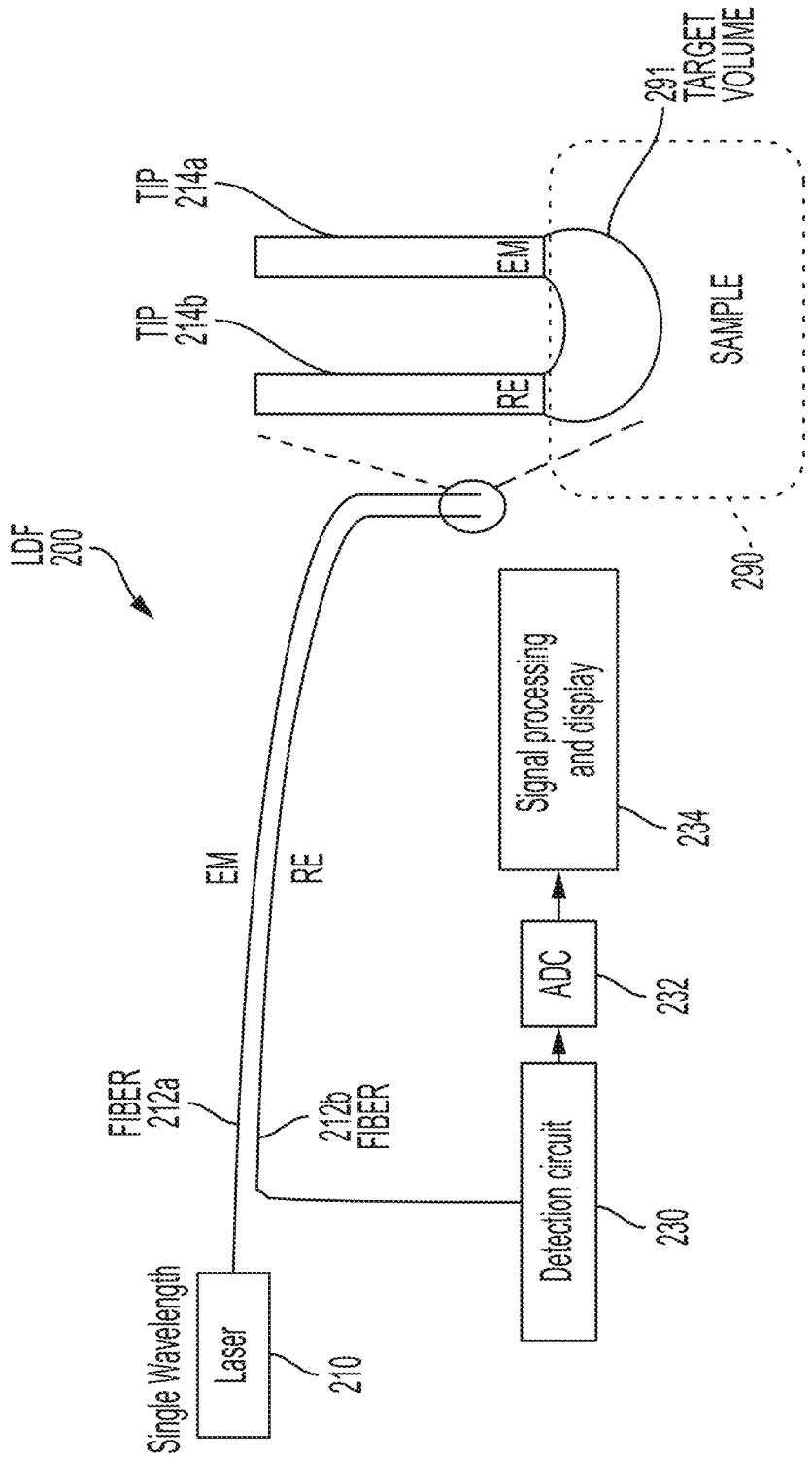
FIG. 2A is a block diagram that illustrates an example laser Doppler flowmetry (LDF) apparatus for detecting fluid flow within tissue.

FIG. 2A is a block diagram that illustrates an example laser Doppler flowmetry (LDF) apparatus 200 for detecting fluid flow within tissue. To illustrate the operation of device 200, a sample 290 is depicted; however, sample 290 is not part of apparatus 200. As used here and throughout, a sample refers to any subject on which a device operates, whether a living organism, including humans, animals and plants, or an excised portion thereof, or some other object, such as a device with moving parts, including moving fluids.

The LDF apparatus 200 includes a narrow bandwidth laser source 210 called a single wavelength laser source, light from which is coupled to optical fiber 212a that terminates in a first probe tip 214a. This light is called emitted light and is signified in FIG. 2A by the letters "EM." In practice, the laser source 210 is not absolutely single wavelength but comprises light in a very narrow wavelength band.

The light from laser 210 exits the tip 214a and interacts with a target volume 291 of the subject 290. The target volume depends on the attenuation of the light at the single wavelength of laser 210 in the subject 290. Light propagating through or scattered from the target volume, or both, enters tip 214b of optical fiber 212b and propagates along fiber 212b from the tip to a detection circuit 230. This light propagating through fiber 212b is called returned light and is signified in FIG. 2A by the letters "RE." The detection circuit outputs an electronic signal, such as current or voltage, proportional to the electric or magnetic field that impinges on a light sensitive portion of the detection circuit 230. In the illustrated embodiment, the signal output by the detection circuit is an analog signal. That signal is passed to the analog to digital converter (ADC) 232 which outputs a digital signal that can be processed by a digital processor, as described below with reference to computer system 1000 in FIG. 10 or chip set 1100 in FIG. 11. Digital signal processing and display components 234 are configured to processes the digital signal and presents the results, such as a graph or listing that indicates a number or speed of scatterers in the target volume 291 for one or more speed intervals at one or more times.

The interference at the detection circuit 230, if any, is caused by a difference between the returns from scatterers in target volume 291 that are not moving and the Doppler shifted returns from moving scatterers in target volume 291. Because the same target volume 291 provides both the Doppler shifted and non-Doppler shifted optical waves (also referred to as photons, the quantum unit of electromagnetic waves), the interference pattern at the detection circuit 230 is said to be homodyne interference. While suitable for many purposes, the target volume is large compared to the features of interest (e.g., blood vessels or microchannels) in many applications. Thus the device 200 indicates whether there is motion in the volume 291 but does not indicate where in the volume the motion occurs. For example, one can determine that blood is flowing through tissue in the target volume but the blood vessels cannot be localized. Also, if there are too many background moving scatterers outside a region of interest or too few non-moving scatterers in the volume, the signal to noise ratio suffers and may render the measurements unreliable.

The target volume 291 is difficult to control because of the long coherence length Lc of the narrowband laser 210. Temporal coherence is a measure of the average correlation between the value of a wave and itself delayed by a time difference $\tau$, at any pair of times and monochromaticity of the light source. In other words, it characterizes how well a wave can interfere with itself at a different time. The delay over which the phase or amplitude wanders by a significant amount (and hence the correlation decreases by significant amount) is defined as the coherence time $\tau c$. At $\tau=0$, the degree of coherence is perfect; whereas, it drops significantly by delay $\tau c$. The coherence length Lc is defined as the distance the wave travels in time $\tau c$. A wave with a longer coherence length is closer to a perfect sinusoidal wave. Wave interference is strong when the paths taken by all of the interfering waves differ by less than the coherence length. Thus, with the long coherence length of the narrowband light source 210, moving and non-moving scatterers throughout a large target volume 291 interfere significantly at detection circuit 230.

To better localize the vessels holding moving fluids in a sample, such as tissue of a living organism, imaging systems have been developed, which use wideband optical sources with short coherence lengths to achieve a very small and well controlled target volume. Such a small target volume is not likely to include a feature of interest, however; so, a scanning mechanism is included to scan a large number of target volumes, which can be presented as pixels or voxels in two dimensional (2D) or three dimensional (3D) images, respectively. One such imager is a DOCT device that requires a light source with a large optical bandwidth (typical bandwidth ≥6% of the center wavelength), a lateral scanning and depth scanning mechanism, and a visual display.

Figure 2B:
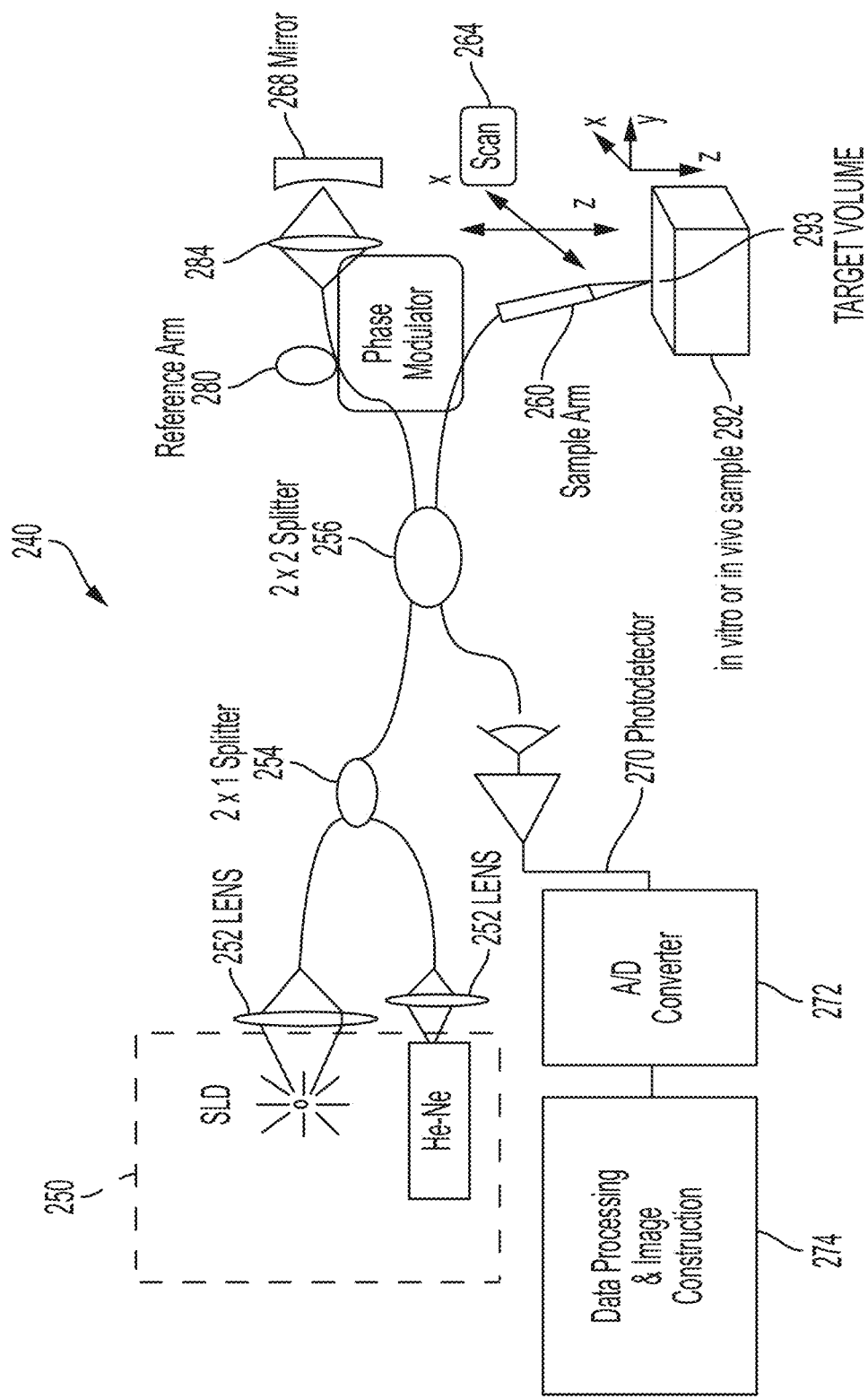
FIG. 2B is a block diagram that illustrates an example Doppler optical coherence tomography (DOCT) apparatus for producing images of fluid flow location within a tissue.

FIG. 2B is a block diagram that illustrates an example Doppler optical coherence tomography (DOCT) apparatus 240 for imaging fluid flow within tissue. This example is taken from Z. P. Chen, T. E. Milner, S. Srinivas, X. J. Wang, A. Malekafzali, M. J. C. vanGemert, and J. S. Nelson, "Noninvasive imaging of in vivo blood flow velocity using optical Doppler tomography," Optics Letters, v22, pp1119-1121, 1997. To illustrate the operation of device 240, a sample 292 is depicted; however, sample 292 is not part of apparatus 240.

The DOCT apparatus 240 includes a wide bandwidth light source 250, such as a superluminescent diode (SLD) to produce power at the scattering frequency of red blood cells combined with a an Helium-Neon (He—Ne) laser for indicating the target volume by a position of a He—Ne laser spot. A SLD combines the high power and brightness of laser diodes with the low coherence of conventional light-emitting diodes. Its emission band is in a range from about 5 nm to about 100 nm wide. Light from this source 250 is coupled by lenses 252 and 2×1 splitter 254 and 2×2 splitter 256 to optical fiber in a sample arm 260. A probe tip at distal end of sample arm 260 directs light into a minute target volume 293 in an in vivo or in vitro sample 292. The probe tip is controlled by a scanning mechanism to scan multiple target volumes 293 in the sample 292. For example, Z. P. Chen et al. state, "Two-dimensional images are formed by sequential lateral scans at a constant horizontal velocity of 800 $\mu m/s$ (micrometers, $\mu m$, also called microns, 1 $\mu m=10^{-6}$ meters, per second), followed by incremental probe movements (10 $\mu m$) in the vertical (axial) direction." The scattered light is returned through the same sample arm to 2×2 splitter 256 which sends a portion to photodetector 270.

Because the target volume 293 is so small and light is scattered diffusely, it is not likely to return sufficient numbers of Doppler shifted and non-Doppler shifted photons from moving and non-moving scatterers, respectively, to generate a useful homodyne interference signal. In this case a reference path is provided through a reference arm optical fiber 280 to provide non-Doppler shifted reference photons with the appropriate mean delay interference at photodetector 270. Because the non-Doppler shifted photons are not from the same target volume 293 as the Doppler shifted photons, if any, this type of interference is called heterodyne interference. A portion of the light from source 250 is coupled into the reference arm by 2×2 splitter 256. Because the signal from source 250 is broadband, its coherence length is very short and to achieve significant interference at photodetector 270 the differences in the path lengths between the returns from the sample arm 260 and the returns from the reference arm 280 must be less than the coherence distance Lc. To match the path distances, the reference arm includes a moveable mirror 286. To avoid confounding homodyne interference with the desired heterodyne interference, the reference light is optionally changed in frequency by phase modulation component 282 so that the difference (and corresponding beat frequencies are much higher, about 10 kHz or greater) is greater than the maximum frequencies generated by blood flow. The reference arm light is directed to the photodetector by 2×2 splitter 256. As stated by P. Chen et al., "Fluid-flow velocity at each pixel is determined by measurement of the Doppler frequency shift, which is defined as the difference between the carrier frequency established by the optical phase modulation and the centroid of the measured power spectrum at each pixel."

The photodetector 270 outputs an electronic signal, such as current or voltage, proportional to the electric or magnetic field that impinges on the photodetector 270. In the illustrated embodiment, the signal output by the photodetector 270 is an analog signal. That signal is passed to the analog to digital converter (ADC) 272 which outputs a digital signal that can be processed by a digital processor. Digital signal processing and image construction components 274 are configured to processes the digital signal and presents the results, such as an image of the locations and amounts of fluid motion, or statistics of same.

Figure 2C:
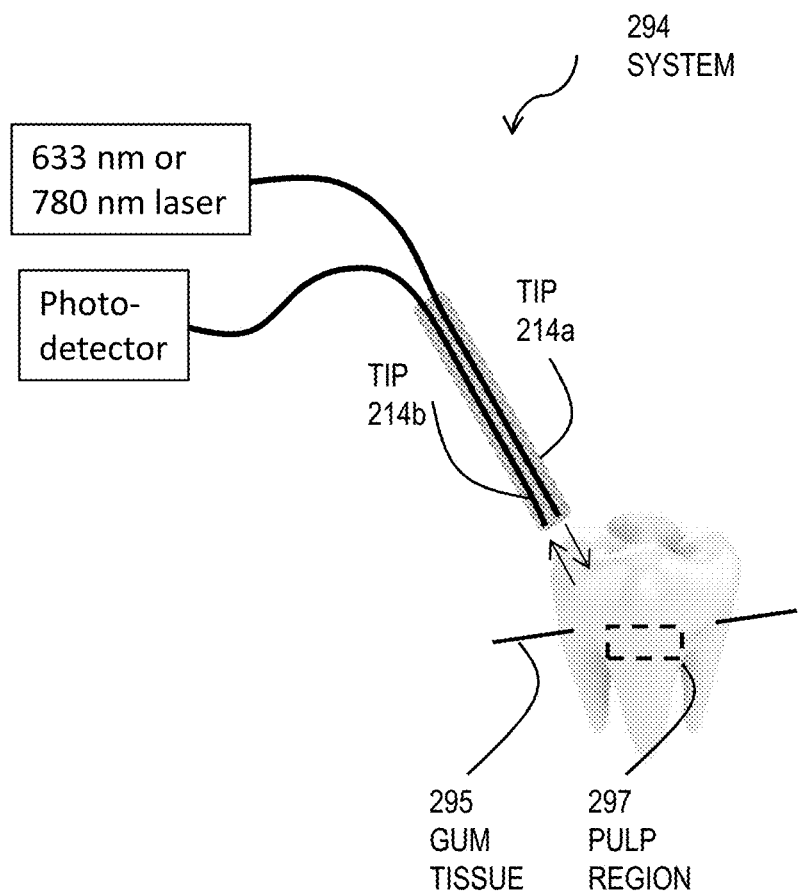
FIG. 2C is a block diagram that illustrates an example laser Doppler flowmetry (LDF) apparatus for detecting fluid flow within tooth pulp.

FIG. 2C is a block diagram that illustrates an example laser Doppler flowmetry (LDF) system 294 for detecting fluid flow within tooth pulp. The system 294 is similar to the LDF system 200 of FIG. 2A except the tips 214a, 214b are positioned at a top surface of the tooth and are spaced close together (e.g. within 0.5 mm). Based on this close spacing of the tips 214a, 214b, the difference in the optical path length from the tip 214a to the pulp region 297 and back to the tip 214b and from the tip 214a to the gum tissue 295 and back to the tip 214b is relatively small and less than the long coherence length of the laser. Consequently, signals from the pulp region 297 and gum tissue 295 interfere at the detector and thus the system 294 cannot distinguish fluid motion within the pulp region 297 from fluid motion within the gum tissue 295. Since the top surface of the pulp region 297 of most adult teeth, except for the small incisors, is located at least 3-4 mm below from the upper tooth surface, only a small fraction of the incident light is Doppler shifted by moving red cells within the blood vessels of the pulp region 297. The top surface of a receding tooth pulp region 297 can be located at or below the gum line, even farther from the top surface of the tooth than the gum tissue 295. The signal to noise ratio of signals from the pulp region 297 is not sufficient to detect fluid motion within the pulp region 297, as a result of motion artifacts received from the gum tissue 295.

The inventors recognized that the sensitivity of fiber optic probe in the system 294 to detecting pulp flow is low and depends on placement of the probe tips 214a, 214b relative to the pulp region 297 and gum tissue 295. Specifically, the inventors recognized that the probe tips 214a, 214b need to be positioned such that the difference in the optical path from the tip 214a to the pulp region 297 and back to the tip 214b and from the tip 214a to the gum tissue 295 and back to the tip 214b is greater than the laser coherence length so that scattered signals from the gum tissue 295 do not interfere at the detector and thus fluid motion within the pulp region 297 is measured while motion artifacts from the gum tissue 295 are suppressed.

1. Overview

The current embodiment includes methods and devices that increase the sensitivity of laser Doppler flowmetry (LDF) to detect pulp blood flow, while rejecting gum blood flow more effectively. In the current embodiment, a novel transmission-mode configuration with an optical reference channel that increases both the interferometric gain and the effective size of the detection aperture achieves a large sensitivity gain. Rejection of gum blood flow is achieved by using a specific optical probe geometry combined with a light source that has a tailored spectral emission profile. An embodiment of an optical tooth vitality testing system includes a user-friendly, low-cost probe with a detachable portion that can be steam sterilized between uses.

Various embodiments are based on a transmission-mode optical configuration that, when combined with other features, mitigates the limitations of low sensitivity and susceptibility to false readings from blood flow in the gums. For example, one embodiment includes a motion sensor that is suitable as a real-time guidance device for medical and other applications.

Figure 3A:
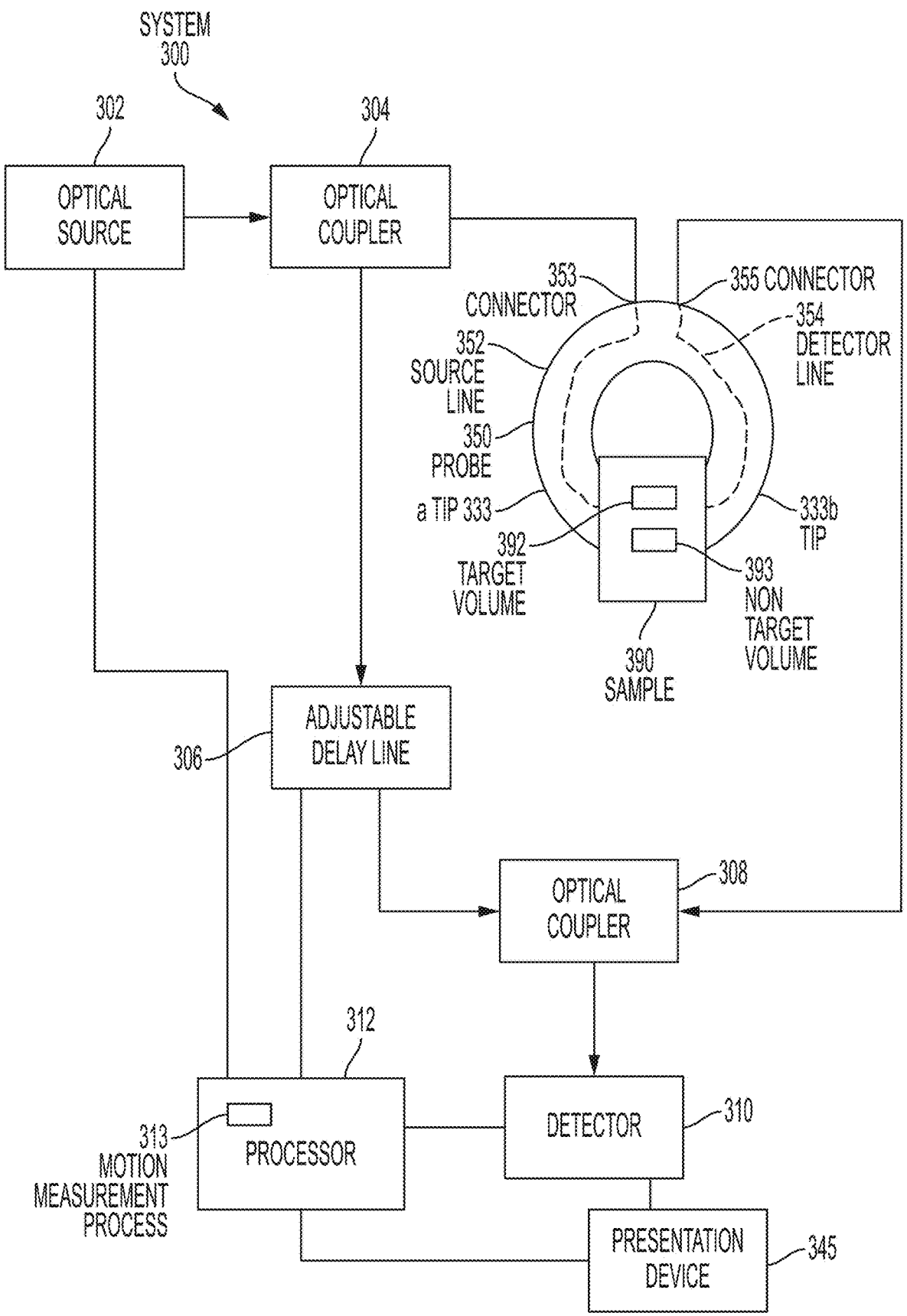
FIG. 3A is a block diagram that illustrates example components of a coherence gated Doppler (CGD) system, according to various embodiments.

FIG. 3A is a block diagram that illustrates example components of a coherence gated Doppler (CGD) system 300, according to various embodiments. To illustrate the operation of system 300, a sample 390 is depicted; however, sample 390 is not part of system 300. The system 300 includes a selected bandwidth optical source 302 that determines both a center wavelength in order to appropriately penetrate a sample 390 and detect scatterers that move with the motion to be detected, and also the coherence length Lc appropriate for a target volume 392 appropriate for the application. In some embodiments, the optical source 302 has an adjustable bandwidth. In other embodiments, the optical source 302 has a fixed or non-adjustable bandwidth. For example, for a hand-held probe, an appropriate target volume 392 is on the order of a cubic millimeter, such as volumes with spot diameters in a range from about 0.1 millimeters (100 microns) to about 5 millimeters. In some embodiments, the sample 390 is a tooth and the target volume 392 is a pulp region within the tooth. In one embodiment, light outputted from the optical source 302 is referred to as output light.

The overall coherence gated sample volume 392 is affected by the dimension and focusing the optical source 302 and detector apertures and the scattering coefficient of the sample. A vertical extent of the coherence gated sample volume 392 is determined, at least in part, by the coherence length Lc. In an embodiment, where the sample 390 is the tooth and the target volume 392 is tooth pulp, to obtain a sufficiently high sensitivity to blood flow in the tooth pulp, while minimizing sensitivity to long path lengths through gum tissue, a wavelength bandwidth of about 0.5 nm or in a range from about 0.25 nm to about 1 nm is advantageous. For good transmission through the tooth, a center wavelength in a range of about 1250 nm to about 1350 nm of about 1550 nm to about 1750 nm is desirable to minimize scattering and absorption losses; however, other wavelengths in the visible or near infrared band can be employed at the expense of signal strength. In another embodiment, inexpensive semiconductor light sources are available at about 1310 nm and thus this wavelength is a good choice with a 0.5 nm bandwidth that corresponds to about 0.04% of the center wavelength. For a shorter center wavelength, the percentage is higher. For many applications, it is advantageous for the bandwidth to be intermediate between that of LDF and DOCT, e.g., for bandwidths in a range from about 0.01% to about 5% of a center wavelength. In some applications, it is preferable for the bandwidth to be in a range from about 0.01% to about 0.10%. In embodiments directed to the detection of blood cells, it is desirable for the bandwidth to be in a range from about 0.02% to about 0.08%. Because the target volume 392 is controlled, at least in part, by the coherence length of the source 310, the volume 392 is called a coherence gated target volume 392 and the system 300 is called a coherence gated Doppler (CGD) device.

The present system is designed to maximize light penetration and to control the size and location of the detection zone. Different types of light sources having various wavelengths may be used. Suitable light sources with selected center wavelength and bandwidth are known in the art. In one embodiment for application to teeth, a Superluminescent Light Emitting Diodes light source (SLED) with a center wavelength of about 1310 nm is used. This differs significantly from a conventional laser Doppler's wavelength of 780 nm because the teeth will not attenuate the longer wavelength infrared light as much. The SLED is also a preferred embodiment because it has a special type of laser diode with wider spectral bandwidth. As stated above, the bandwidth controls the coherence length which in turn controls the detection volume. Besides SLED, it is also possible to use a white light laser with suitable bandpass filter or semiconductor laser with appropriate bandwidth.

The device also includes an optical detector 310 that outputs an electronic signal, such as a digital or analog current or voltage, which indicates the optical interference pattern at the detector. Example detectors include a photodiode, an Indium gallium arsenide (InGaAs) photodetector, a balanced detector, a charge-coupled device (CCD) and a Complementary metal-oxide-semiconductor (CMOS) photodetector. In some embodiments, a dual balanced detector is employed as detector 310 to improve signal to noise ratio by reducing common mode noise.

The output light emitted from source 302 is directed into a probe 350 including tips 333a, 333b that engage opposite sides of the sample 390. A first tip 333a of the probe 350 engages a first side of the sample 390 and a second tip 333b of the probe 350 engages a second opposite side of the sample 390. In an embodiment, a pair of fiber optic lines pass through an interior of the probe 350 and include a source line 352 that is a fiber optic line which terminates at a distal end in the tip 333a. In an embodiment, the fiber optic line serving as the source line 352 is single mode or predominantly single mode. In other embodiments, the fiber optic line serving as the source line 352 is multi mode. In various embodiments, the distal end of the source line 352 is a simple perpendicular cut of the optical fiber serving as the source line 352 or an angled cut of the fiber serving as the source line 352 to control the back reflection power from the end surface, or a shaped end of the fiber to control the back reflection power from the end surface, or a coated end surface of the fiber to control the back reflection power from the end surface, or a Gradient-index (GRIN) multimode fiber to serve as a lens, or a GRIN rod lens, or ball lens, or a micro-lensed fiber or is a stiff needle connected to the source line 352, or includes a lens or collimator, or a coating or other optical coupler, or some combination. The distal end of the source line 352 emits output light from source 302 and directs it onto a spot in or on the sample 390. In some embodiments, an angled surface within the tip 333a of the probe 350 redirects the output light emitted from the source line 352 in the sample 390. In some embodiments, the probe 350 is configured to be held in a hand of a user or clamped on the surface of the tooth.

A source line connector 353 is an optical connector that is configured to couple light received directly or indirectly (e.g., through optical coupler 304) from the source 302 into the source line 352. As used herein the term connector refers to any components or configuration of components that serve to direct light from one region (point, area or volume) of space to another region of space, and includes, among others, a free space vacuum, a gas or liquid filled free space, a crystal, a lens, Gradient-index (GRIN) optical component, such as a GRIN lens, a fiber bundle, a fiber coupler (FC), a beam splitter, a circulator, an optical fiber, a mirror, or any combination.

The pair of fiber optic lines in the probe 350 also includes a detector line 354 that is a fiber optic line which terminates at a distal end in the tip 333b. In an embodiment, the fiber optic line serving as the detector line 354 is multi mode or predominantly multi mode. In another embodiment, the fiber optic line serving as the detector line 354 is single mode. In various embodiments, the distal end of the detector line 354 is a simple perpendicular cut of the optical fiber serving as the detector line 354 or an angled cut of the fiber serving as the detector line 354 or a coated end surface of the fiber or a Gradient-index (GRIN) multimode fiber to serve as a lens, or a GRIN rod lens or ball lens or a micro-lensed fiber or is a stiff needle connected to the detector line 354 or includes a lens or collimator or a coating or other optical coupler or some combination. In an embodiment, the distal end of the detector line 354 receives scattered light from the target volume 392 and directs the scattered light to the detector 310 through an optical coupler 308.

A detector line connector 355 is configured to couple scattered light from the detector line 354 directly or indirectly (e.g., through optical coupler 308) into the detector 310.

The scattered light returned from sample 390 is captured by the detector line 354 at probe tip 333b. As is the case for probe tip 333a, in various embodiments, the probe tip 333b can take various forms. In some embodiments, the probe tip 333b is configured to be held in a hand of a user. It is advantageous if the probe tip 333b and probe tip 333a are configured to form opposing surfaces of the probe 350 (e.g. caliper tips).

In some embodiments, heterodyne interference is utilized and a reference path is introduced to direct a portion of the output light from the source 302 onto the optical detector 310. In such embodiments, optical coupler 304 is included to direct a portion of the output light from the source 302 to an adjustable delay line 306 in the reference path, to an optical coupler 308 and the optical detector 310. The configuration of the fiber couplers of the systems depend on the purpose of the system. Variations in the distribution of the laser power between the emitted light path directed to the source line 352 and the reference path directed to the adjustable delay line 306 will be application specific. In one example embodiment, the optical coupler 304 distributes 10% of laser power to the adjustable delay line 306 and the other 90% to the source line 352. In other example embodiments, the laser power distributed to the probe 350 can be between about 99% and about 1%. For medical use, the preferred power expelled by the probe tip 333a should not exceed the United States Food and Drug Administration (FDA) recommendation. The optical probe tip 333a is capable of focusing the laser beam in a perpendicular direction at different sizes. In one example, the beam is focused to a spot size of 40 μm at a distance 1.5 mm away from the probe 350. However, in other uses, the spot size and distance may be more or less. The size of the target volume in the axial direction of propagation is at least in part determined, as described, above, by the coherence length Lc.

In some embodiments, the adjustable delay line 306 includes a path length correction component so that a zero delay plane is positioned at the target volume 392 within the sample 390. The zero-delay plane is defined as the plane in the target volume 392 which has the same optical path length to detector 310 as the optical path length through the reference path (e.g. adjustable delay line 306) to detector 310. Since the signal from the target volume 392 (defined by the coherence length Lc) surrounding the zero-delay plane is higher than signal from other regions including non-target volume 393, the position of the zero-delay plane can be set by the reference path length to highlight the target volume 392 within the sample 390. In some embodiments, the reference path length correction is adjustable so that the depth of the target volume 392 within the sample 390 can be adjusted. In an embodiment, the path is preset for a predetermined depth within the sample 390. This embodiment is advantageous because the user does not have to make the adjustment, which renders the device simpler to use and frees the user's hands for other actions. Furthermore, the mechanism to adjust the path length can be omitted, making the device more stable, less susceptible to vibration or orientation, smaller, lighter, and cheaper to build.

Figure 10:
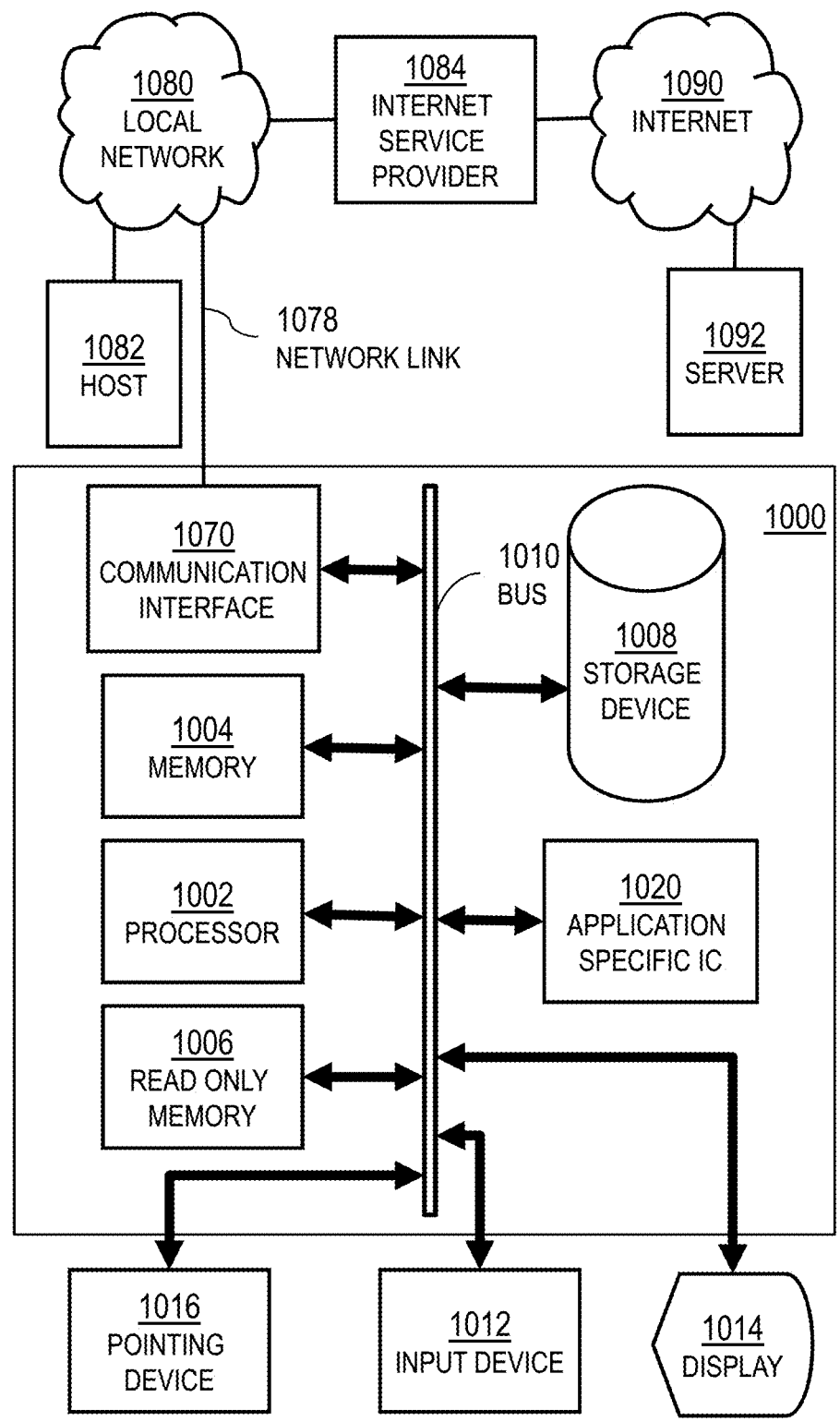
FIG. 10 is a block diagram that illustrates a computer system upon which an embodiment of the invention may be implemented.
Figure 11:
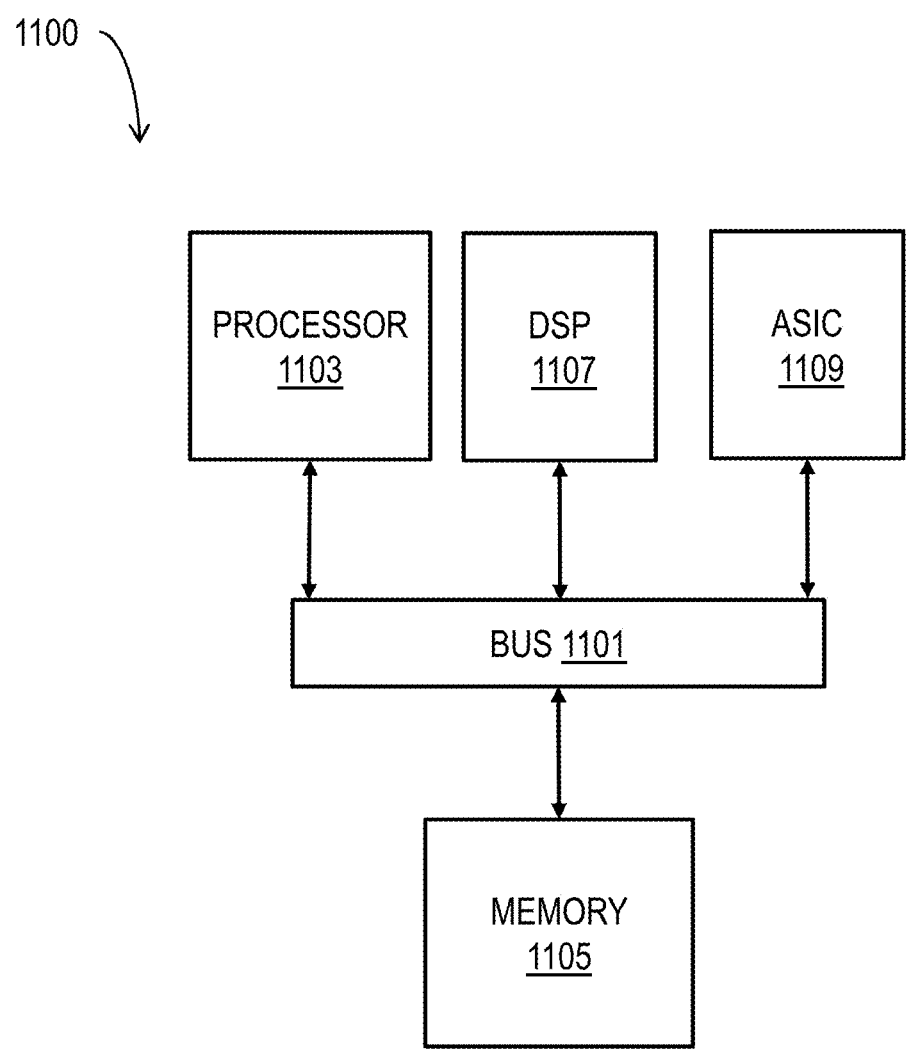
FIG. 11 is a block diagram that illustrates a chip set upon which an embodiment of the invention may be implemented.

Electronic output from detector 310 is passed to a processor 312 to measure motion (e.g. flow of blood cells) within the target volume 392 based on a Doppler shift in a signal received at the detector 310 from the target volume 392 relative to the signal received at the detector 310 from the reference path. In some embodiments, an analog-to-digital converter (ADC) is positioned between the detector 310 and processor 312 to convert an analog signal from the detector 310 into a digital signal that is received by the processor 312. The processor 312 includes a motion measurement process module 313 to perform one or more steps of a method described below with reference to FIG. 4. In various embodiments, the processor 312 comprises one or more general purpose computer systems, as depicted in FIG. 10 or one or more chip sets as depicted in FIG. 11 and instructions to cause the computer or chip set to perform one or more steps of a method described below with reference to FIG. 4. In some embodiments, an ADC is not used and an analog output from the detectors is presented at an analog device, such as an acoustic speaker. In such embodiments, a trained operator can determine qualitatively the blood flow within the pulp, and the health of the tooth, based on the frequency of the sound heard from the speaker.

In some embodiments, the system 300 includes a presentation device 345 that indicates to a user the motion (amount of scatterers, speed of scatterers, or direction of scatterers, or some combination) in a coherence gated target volume 392 of sample 390. Any presentation device may be used. In some embodiments, the presentation device 345 includes a digital port with digital output based on the electronic signal from optical detector 310, which digital output may be used by the processor 312 (e.g. computer system 1000) to display or speak one or more values that characterize the motion in target volume 392. In some embodiments, the presentation device 345 is an acoustic speaker that emits an acoustic signal that depends on the output of optical detector 310.

In some embodiments direction of flow is inferred by rotating the probe tip in the vicinity of the sample. As the probe tip encounters more of the approaching flow, the frequency should increase; and, conversely as the probe tip encounters more of a receding flow the frequency should decrease. Thus, a direction of flow can be determined, at least qualitatively, by the dependence of frequency detected on the angle of the probe tip.

Some combinations of features described above reduce cost and improve sensitivity enough to allow detection of flow in blood vessels of various sizes using a handheld probe with no moving parts. In various embodiments, CGD is also less dependent on the relative angle between the probe and the blood vessel because, unlike conventional Doppler flow imaging, interference over long optical paths generates fluctuating speckle patterns that can be detected audibly even when vessels are probed at a 90 degree angle.

There are a number of applications that would benefit from the system described herein. The improvements outlined above, in various embodiments, enable the applications of CGD to detection of blood vessels during instrument insertion for stereotactic neurosurgery; detection and avoidance of large blood vessels during anesthesia injection, catheterization, cerebrospinal fluid collection procedures, intravascular interventions or non-vascular interventions, vessel avoidance in the brain during deep brain electrode placement, tooth pulp vitality detection (with rejection of adjacent flow in the gums), and verification of flow cessation in ligated vessels during open surgical procedures.

These devices and systems are not limited to medical use. The sensors may be designed to be used with engines or other instruments, such as microfluidic devices and micro-electro-mechanical systems (MEMS), where it is important to monitor or detect flow.

Figure 3B:
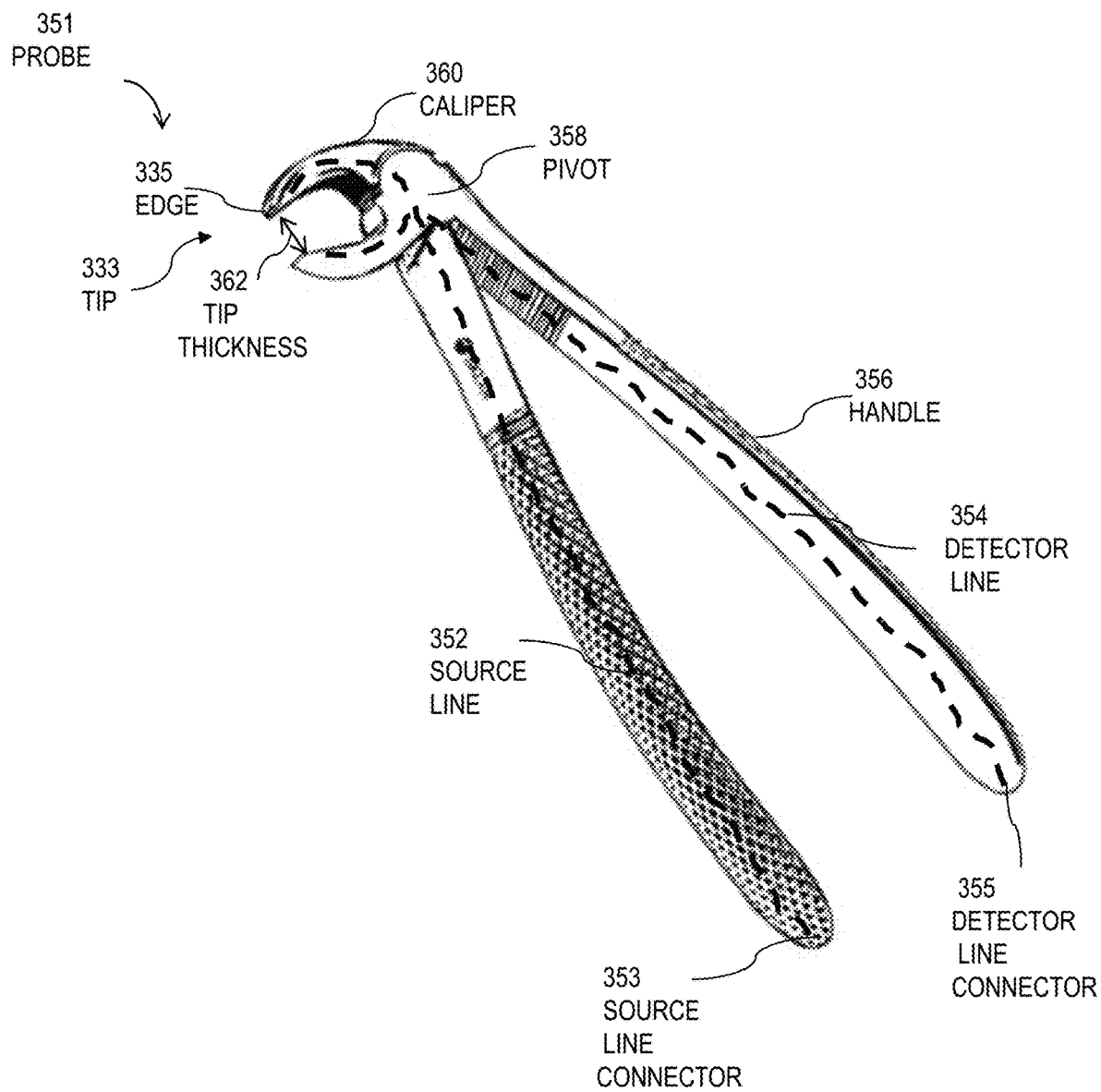
FIG. 3B is a block diagram that illustrates example components of an apparatus used in the system of FIG. 3A, according to various embodiments.

FIG. 3B is a block diagram that illustrates example components of an apparatus used in the system 300 of FIG. 3A, according to various embodiments. In an embodiment, the apparatus is a probe 351 that is used as the probe 350 in the system 300. In an embodiment, the probe 351 takes the form of dental extracting forceps. The probe 351 includes a handle 356, a pivot 358 and a caliper 360, where the handle 356 and caliper 360 are pivotally rotatable about the pivot 358. In one embodiment, the handle 356 and caliper 360 are integral.

In one embodiment, the source line 352 passes through an interior of the handle 356, around or through the pivot 358, and through the caliper 360. In another embodiment, the source line 352 passes along an exterior surface of one side of the handle 356, an exterior surface of the pivot 358 and over an exterior surface of the caliper 360 to the tip 333. In an embodiment, the source line 352 is single mode or predominantly single mode. In one embodiment, the source line 352 is single mode at least in the handle 356. The source line connector 353 is positioned at the end of the source line 352 and is configured to receive output light from the optical source 302 (through optical coupler 304). In an example embodiment, output light from the optical source 302 is transmitted through a single mode fiber (SMF) to the connector 353 that is a single mode to single mode connector.

In one embodiment, the Single Mode Fiber (SMF) is an optical fiber designed to carry light only directly down the fiber—the transverse mode. Modes are the possible solutions of the Helmholtz equation for waves, which is obtained by combining Maxwell's equations and the boundary conditions. These modes define the way the wave travels through space, i.e. how the wave is distributed in space. Waves can have the same mode but have different frequencies. This is the case in single-mode fibers, where we can have waves with different frequencies, but of the same mode, which means that they are distributed in space in the same way, and that gives us a single ray of light. In one embodiment, the SMF has a core diameter between 8 and 10.5 µm and a cladding diameter of 125 µm. There are a number of special types of single-mode optical fiber which have been chemically or physically altered to give special properties, such as dispersion-shifted fiber and nonzero dispersion-shifted fiber. Data rates are limited by polarization mode dispersion and chromatic dispersion.

In another embodiment, the single mode to single mode connector is used to join single mode optical fibers where a connect/disconnect capability is required. In one embodiment, the single mode to single mode connector is a connector assembly. A connector assembly consists of an adapter and two connector plugs. Due to the sophisticated polishing and tuning procedures that may be incorporated into optical connector manufacturing, connectors are generally assembled onto the optical fiber in a supplier's manufacturing facility. However, the assembly and polishing operations involved can be performed in the field, for example to make cross-connect jumpers to size.

The detector line 354 also passes through an interior of the handle 356, around or through the pivot 358, and through the caliper 360. The detector line 354 is multi mode or predominantly multi mode fiber. In one embodiment, the detector line 354 is a 50-µm or 62.5 µm graded-index low-dispersion telecommunications fiber. The detector line connector 355 is an optical connector that is positioned at the end of the detector line 354 and is configured to transmit scattered light from the detector line 354 to the detector 310 (through optical coupler 308). In an example embodiment, scattered light from the detector line 354 is transmitted to the optical coupler 308 over a multi mode fiber (MMF) that is connected to the connector 355, such that the connector 355 is a multi mode to multi mode connector.

In one embodiment, the Multi Mode Fiber (MMF) is a type of optical fiber mostly used for communication over short distances. Typical multi-mode links have data rates of 10 Mbit/s to 10 Gbit/s over link lengths of up to 600 meters (2000 feet). In an embodiment, the Multi-mode fiber has a fairly large core diameter that enables multiple light modes to be propagated and limits the maximum length of a transmission link because of modal dispersion. The main difference between multi-mode and single-mode optical fiber is that the former has much larger core diameter, typically 50-100 micrometers; much larger than the wavelength of the light carried in it. Because of the large core and also the possibility of large numerical aperture, multi-mode fiber has higher "light-gathering" capacity than single-mode fiber. In one embodiment, the Multi-mode fiber is described based on the core and cladding diameters. In one example embodiment, a 62.5/125 µm multi-mode fiber has a core size of 62.5 micrometres (µm) and a cladding diameter of 125 µm. The transition between the core and cladding can be sharp, which is called a step-index profile, or a gradual transition, which is called a graded-index profile. The two types have different dispersion characteristics and thus different effective propagation distance. Multi-mode fibers may be constructed with either graded or step-index profile.

The tip 333 of the probe 351 has a thickness 362 that is sized such that output light from the source line 352 is emitted from the tip 333 within a threshold distance of an edge 335 of the tip 333. In an embodiment, the threshold distance is about 0.5 mm or within a range from about 0 mm to about 0.7 mm of the edge 335 of the tip 333. In an example embodiment, a tip separation measurement is provided between opposing sides of the handle 356 which indicates a separation distance of the opposing sides of the handle 356. In an example embodiment, a separation distance indication on the tip separation measurement correlates with a thickness 362 of the tip 333 of the caliper 360.

FIG. 3C is a block diagram that illustrates example components of an apparatus used in the system 300 of FIG. 3A, according to various embodiments. In an embodiment, the apparatus is a probe 351' that is used as the probe 350 in the system 300. In an embodiment, the probe 351' is similar to the probe 351 with the exception of the features discussed herein. The caliper 360' of the probe 351' is removably attached to the handle 356'.

In one embodiment, the probe 351' is configured to measure pulp flow in a variety of tooth types, and for convenient and low-cost use in dental practice. In some embodiments, the probe 351' is fabricated from metal, ceramic, or a high-temperature plastic (e.g., PEEK™ from Curbell Plastics, Orchard Park, NY). In an embodiment, the probe 351' includes a tapered tip, body, handles, and connectors. The tapered tip has a shape that is similar to a typical tooth extractor, for example. In one embodiment, the tapered tip is configured to reduce measured motion of the tapered tip relative to the tooth. For example, the tapered tip may be configured to clamp on the tooth or be temporarily fixed to a tooth by an adhesive, or the like.

In an embodiment, the source line 352' includes a single mode fiber (SMF) 370a in the handle 356' and a multi mode fiber (MMF) 372a in the removable caliper 360'. A single mode to multi-mode fiber connector 374a is positioned between the caliper 360' and the handle 356' and is used to couple light from the SMF 370a in the handle 356' to the MMF 372a in the caliper 360' when the caliper 360' is attached to the handle 356'. The connector 374a advantageously features a single mode to multi mode connector, in order to loosen alignment tolerance and therefore, maximize the amount of light that is coupled from the source line 352' in the handle 356' to the source line 352' in the caliper 360'. This connector 374a advantageously permits the tip 333' and caliper 360' to be detachable from the handle 356'. The removable tip 333' and caliper 360' facilitate sterilization or disposal of the tip 333' between uses. In one embodiment, the tip 333' is disposable after use and replaced with a new sterilized tip 333' for subsequent use. In another embodiment, the removable tip 333' is sterilized using a sterilized solution or autoclave for a predetermined time period, as appreciated by one of ordinary skill in the art. After the removable tip 333' is sterilized it is replaced on the handle 356' and reused. In the illustrated embodiment the pivot 358' is included in the removable tip 333'. In some embodiments, the pivot 358' is included in the reusable handle 356' and not in the removable tip 333', and two removable tips are used—one for the source line caliper and one for the detector line caliper.

In an embodiment, the detector line 354' includes a multi mode fiber (MMF) 370b in the handle 356' and a multi mode fiber (MMF) 372b in the caliper 360'. A multi mode to multi mode connector 374b is positioned between the caliper 360' and the handle 356' and is used to couple light from the MMF 370b in the handle 356' to the MMF 372b in the caliper 360' when the caliper 360' is attached to the handle 356'.

In one embodiment, the tip 333' is configured to be removable and disposable. For example, in one embodiment the tip 333' is low-cost such that replacement of each tip due to wear and sanitation or hygiene requirements is cost effective. In another embodiment, the tip 333' is configured to be removable and disposable and includes the light source, such as an integrated photonic circuit or laser-on-a-chip, or the like.

In an embodiment, the tip 333' of the caliper 360' is arranged so that output light from the source line 352' is emitted from the tip 333' at a predetermined angle relative to a longitudinal axis 376 of the tip 333'. In one embodiment, the predetermined angle is about 90 degrees or in a range from about 80 degrees to about 100 degrees. In one embodiment, the longitudinal axis 376 is defined by the caliper 360' at the tip 333'. In one embodiment, the caliper 360' includes an angled surface 377 at the tip 333' that is oriented to reflect or redirect light from the source line 352' at the predetermined angle relative to the longitudinal axis 376. In an example embodiment, the angled surface 377 is formed by polishing the tips of the fibers at about 45 degrees or in a range from about 30 degrees to about 60 degrees relative to the longitudinal axis 376 so that the light is redirected by total internal reflection. Alternatively, a separate lens/reflector assembly can be fabricated from plastic, glass or other transparent ceramic. FIG. 3D is a block diagram that illustrates the example source line 352' of the apparatus of FIG. 3C, according to various embodiments. In an embodiment, the tip of the optical fiber 357 forming the source line 352' is melted and then polished at about 45 degrees relative to the longitudinal axis 376. The angled surface 377 is a mirrored surface positioned on the end of the optical fiber 357 to redirect the light within the tip 333b' into the tooth 551 at the predetermined angle relative to the longitudinal angle 376 of the tip 333b'. In one embodiment, the tip 333a' includes an optical fiber 357 that features an angled surface 377 at an end of the optical fiber 357 to redirect the scattered light into the detector line 354' that is similar to the angled surface 377 of the source line 352'.

In one embodiment, the probe 351' is fabricated of an inexpensive glass molding and polishing to withstand the harsh conditions of high-temperature sterilization. In an embodiment, the body of the probe 351' includes hollow channels that embed the optical fibers 370, 372. The connectors 353, 355 are integrally formed with the handle 356' to allow a patient-contacting portion of the probe 351' (e.g. tip 333' or caliper 360') to be steam-sterilized between uses without damaging the optical fibers 370, 372 and strain relief and protective plastic jacket 373.

In some embodiments, the single source line 352 or 352' serves as both emission path to direct output light from the light source 302 onto the sample 390 through the tip 333 and return path to capture scattered light from the sample 390 through the tip 333 and direct it to the optical detector 310 through an optical circulator. In some of these embodiments, the probe tip 333, 333' has a single tip rather than a dual tip.

FIG. 4 is a flowchart that illustrates an example of a method 400 for detecting tooth pulp vitality, according to various embodiments. Although steps are depicted in FIG. 4 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. In step 401, opposite sides of the sample 390 are engaged with the tip 333a, 333b of the probe 350. In an embodiment, the opposite sides of the sample 390 are engaged with the tips 333a, 333b of the probe 350 so that the optical path length difference between the tips 333a, 333b through the target volume 392 and between the tips 333a, 333b through the non-target volume 393 is greater than the coherence length of the optical source 302. In another embodiment, the opposite sides of the sample 390 are engaged with the tips 333a, 333b so that the optical path length difference is greater than one half of the coherence length of the optical source 302.

Figure 5A:
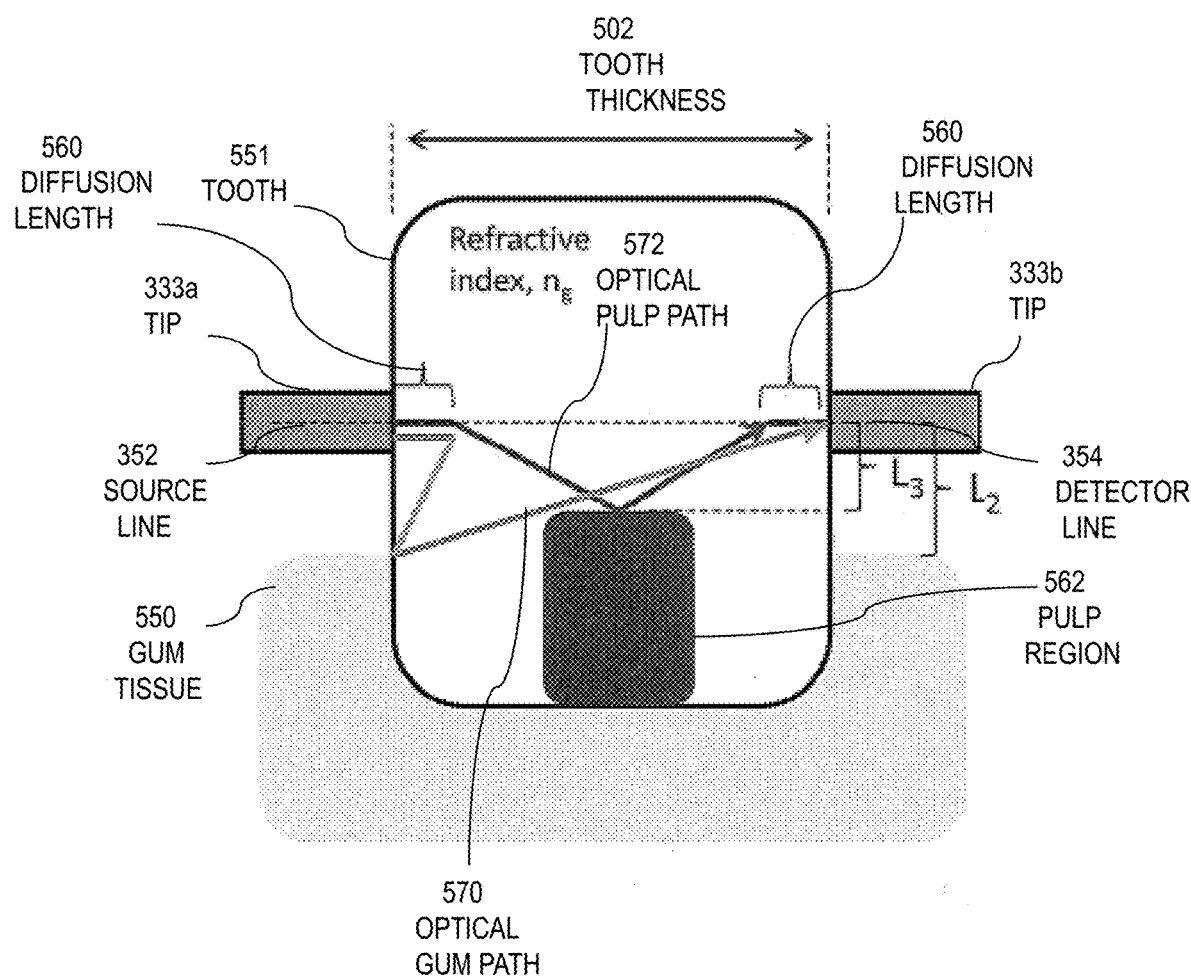
FIG. 5A is a block diagram that illustrates an example of positioning of a tip of the probe on opposite sides of a tooth in the system of FIG. 3A, according to various embodiments.

In an embodiment, in step 401, opposite sides of a tooth are engaged with the tip 333 of the probe 351 or the tip 333' of the probe 351'. FIG. 5A is a block diagram that illustrates an example of positioning of a tip 333 of the probe 351 on opposite sides of a tooth 551 in the system 300 of FIG. 3A, according to various embodiments. A first tip 333a of the probe 351 engages a first surface of the tooth 551 and a second tip 333b of the probe 351 engages a second surface of the tooth 551 that is opposite from the first surface. In an embodiment, the first tip 333a and second tip 333b engage the tooth 551 so that the source line 352 and detector line 354 are positioned within a minimum distance $L_2$ of gum tissue 550 surrounding the tooth 551. In an embodiment, the first tip 333a and second tip 333b engage the tooth 551 so that the source line 352 and detector line 354 are positioned within a minimum distance $L_3$ of pulp region 562 within the tooth 551. Although FIG. 5A depicts that the tip 333a does not engage the gum tissue 550, in some embodiments the tip 333a engages the gum tissue 550 and presses the gum tissue 550. In one embodiment, the minimum distance $L_2$ is about 0.5 mm or in a range from about 0 mm to about 2 mm Additionally, in another embodiment, contours of the tip 333a, 333b are shaped to conform well to contours of the tooth 551.

FIG. 5A depicts an optical path 572 of light between the tips 333a, 333b through the tooth 551 that scatters from the pulp region 562. The optical path 572 includes an initial diffusion length 560 where light incident from the source line 352 propagates in a straight direction within the tooth 551 after which the light deviates and is scattered from the pulp region 562 after which the light propagates along the diffusion length 560 before exiting the tooth 551 and entering the detector line 354.

FIG. 5A also depicts an optical path 570 of light between the tips 333a, 333b through the tooth 551 that scatters from gum tissue 550 surrounding the tooth 551. In one embodiment, for purposes of this description, gum tissue 550 is defined as including one or more of gingival tissue, gingival margin, and periodontal ligament. The optical path 570 includes the initial diffusion length 560 after which the light backscatters and exits the tooth 551 before being scattered by the gum tissue 550 back into the tooth 551 and entering the detector line 354. In an embodiment, the optical path 570 through the gum tissue 550 is greater than the optical path 572 through the pulp region 562 since light backscatters to the gum tissue 550, exits the tooth 551, scatters from the gum tissue 550 and reenters the tooth 551 before entering the detector line 354.

Figure 5B:
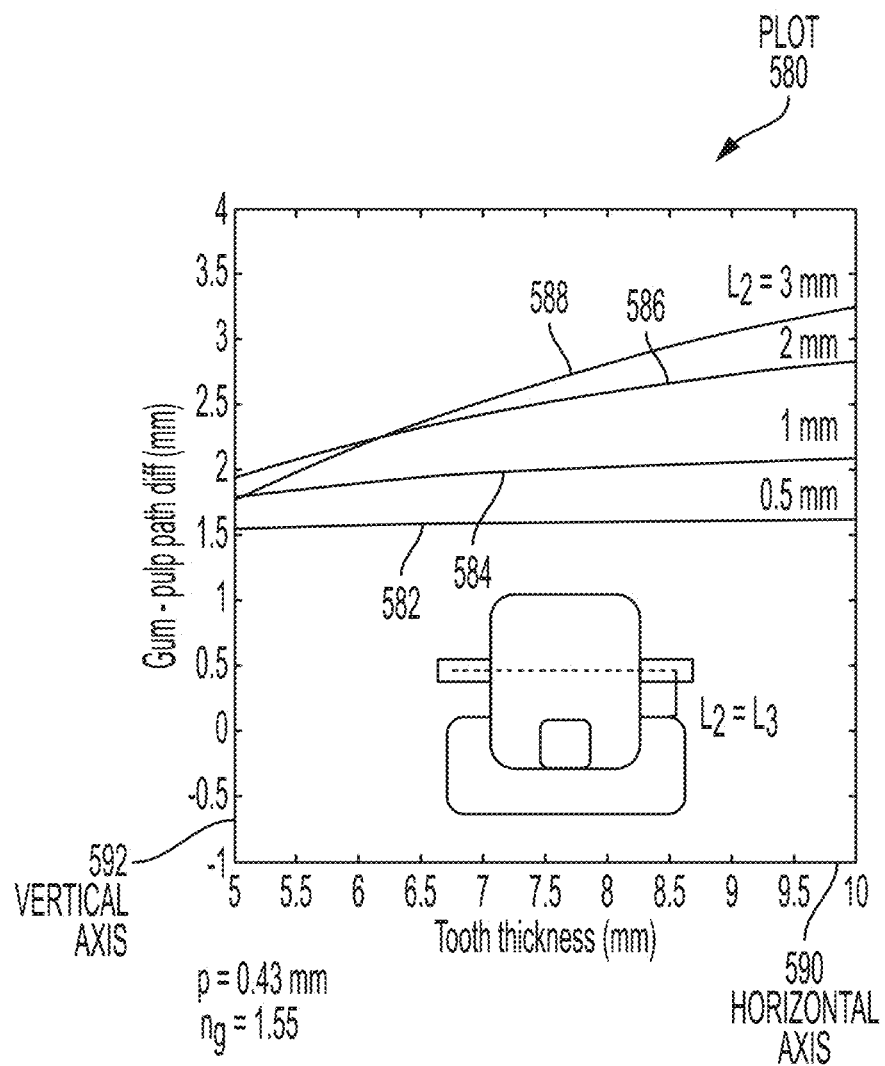
FIG. 5B is a plot that illustrates an example of traces indicating an optical path difference between pulp region and gum tissue for various spacing between the probe and gum tissue, according to various embodiments.

FIG. 5B is a plot 580 that illustrates example traces indicating an optical path difference between pulp region and gum tissue for various spacing between the probe and gum tissue, according to various embodiments. The horizontal axis 590 is thickness 502 of the tooth 551 and represented in units of millimeters (mm). The vertical axis 592 is a difference between the optical gum path 570 and optical pulp path 572 and represented in units of millimeters (mm). For purposes of the traces in FIG. 5B, the diffusion length 560 is about 0.43 mm, the index of refraction of the tooth 551 is about 1.55 and the minimum distance $L_2$ of the gum tissue is about equal to the minimum distance $L_3$ of the pulp region. Trace 582 shows the difference between the optical gum path 570 and optical pulp path 572 where the minimum distance $L_2$ (separation between the tip 333a, 333b and gum tissue 550) is about 0.5 mm Trace 584 shows the difference between the optical gum path 570 and optical pulp path 572 where the minimum distance $L_2$ (separation between the tip 333a, 333b and gum tissue 550) is about 1 mm Trace 586 shows the difference between the optical gum path 570 and optical pulp path 572 where the minimum distance $L_2$ (separation between the tip 333a, 333b and gum tissue 550) is about 2 mm Trace 586 shows the difference between the optical gum path 570 and optical pulp path 572 where the minimum distance $L_2$ (separation between the tip 333a, 333b and gum tissue 550) is about 3 mm. The traces 582, 584, 586, 588 demonstrate that the difference between the optical gum path 570 and optical pulp path 572 across multiple tooth thicknesses 502 and multiple spacings ($L_2$) between the tips 333a, 333b and gum tissue 550 is greater than about 1.5 mm.

In an embodiment, in step 401 the tips 333a, 333b engage the surface of the tooth 551 so that the path difference between the optical gum path 570 and optical pulp path 572 is greater than the coherence length of the optical source 302 so that scattered signals from the gum tissue 550 do not interfere at the detector 310 and thus motion artifacts from the gum tissue 550 are suppressed. In an embodiment, in step 401 the tips 333a, 333b engage the surface of the tooth 551 so that the path difference between the optical gum path 570 and optical pulp path 572 is greater than one half of the coherence length of the optical source 302. In an embodiment, in step 401 the tips 333a, 333b engage the surface of the tooth 551 at a separation ($L_2$) of about 0.5 mm above the gum tissue 550 such that the minimum path difference between the optical gum path 570 and optical pulp path 572 (e.g. at least 1.5 mm) is greater than half of the coherence length of the optical source 302 (e.g. about 3 mm).

In an embodiment, in step 402, output light is emitted from the optical source 302 with an adjustable bandwidth. In other embodiments, output light is emitted from the optical source 302 with a fixed bandwidth. A first portion of the output light is coupled into the source line 352 through the source line connector 353 and a second portion of the output light is coupled into the reference path including the adjustable delay line 306. In one embodiment, in step 402 the optical coupler 304 directs the first portion of output light (e.g. 90%) to the source line connector 353 and the second portion of output light (e.g. 10%) to the adjustable delay line 306 in the reference path.

In an embodiment, in step 404, the second portion of output light is received at the detector 310 from the reference path (e.g. through the optical coupler 308) and scattered light from the detector line 354 is received at the detector 310 from the detector line connector 355 (e.g. through the optical coupler 308).

In an embodiment, in step 406, the adjustable delay line 306 is varied so that a zero delay plane is positioned in the target volume 392 (e.g. pulp region 562 of the tooth 551). In an embodiment, the zero delay plane is defined such that the optical path of output light through the reference path to the detector 310 is equal to an optical path from the zero delay plane through the detector line 354 to the detector 310. In one embodiment, in step 406 the processor 312 receives an interference signal from the detector 310 and analyzes the interference signal. Based on this analysis, the processor 312 transmits a signal to the adjustable delay line 306 to vary the zero delay plane to be within the target volume 392 or within a center of the target volume 392. In an example embodiment, the magnitude of the interference signal in different frequency bands can be used to determine the mean optical path delay through the tooth 551, as well as the delay at which the Doppler power from cardiac pulsations is maximized.

In an embodiment, in step 408, the bandwidth of the output light is adjusted to vary the coherence length of the output light from the optical source 302 so that scattered light from the target volume 392 (e.g. pulp region 562) generates an interference signal at the detector 310 and scattered light from the non-target volume 393 (e.g. gum tissue 550) does not generate an interference signal or generates an interference signal less than a threshold intensity at the detector 310. In one embodiment, in step 408 the processor 312 receives an interference signal from the detector 310 and analyzes the interference signal. Based on this analysis, the processor 312 transmits a signal to the optical source 302 to vary the bandwidth of the output light so that interference signals from the non-target volume 393 are suppressed. In one embodiment, coherence is maintained over a range of optical paths defined by:

$$R = \langle l \rangle \pm \frac{l_c}{2} \qquad (2)$$

where R is the range of optical paths that generate interference signals at the detector 310; <l> is the mean optical path from the zero delay plane to the detector 310 and $l_c$ is the coherence length of the optical source 310. In an embodiment, in step 408 the coherence length $l_c$ is adjusted so that the ratio $l_c/2$ is less than the path difference (e.g. about 1.5 mm) between the optical gum path 570 and the optical pulp path 572 so that scattered light from the gum tissue 550 is suppressed at the detector 310 and does not generate an interference signal. In an example embodiment, in step 408 the coherence length $l_c$ is adjusted to be less than about 3 mm or in a range from less than about 2 mm to less than about 4 mm. In other embodiments, the bandwidth of the output light is fixed and thus the coherence length is preset so that the ratio $l_c/2$ is less than the path difference between the optical gum path 570 and the optical pulp path 572 so that scattered light from the gum tissue 550 is suppressed at the detector 310.

In some embodiments, although other light sources, such as a superluminescent diode, with a very short coherence length can exclude undesired optical paths through the gum tissue 550, these light sources generally generate insufficiently strong interference signals. In an example embodiment, if the coherence length of a light source is too short, the volume of tissue probed by photons that penetrate the pulp region 562 may be too small to generate detectable Doppler signals. In addition, to attain adequate sensitivity, the aperture of the detector fiber must be wide enough to collect diffusely forward-scattered light.

In an embodiment, in step 410, the processor 312 determines motion within the target volume 392 (e.g. pulp region 562) based on the interference signal received from the detector 310. In one embodiment, in step 410 the processor 312 determines a flow of blood cells within the target volume 392 based on a Doppler shift between the scattered light from the pulp region 562 and the output light through the reference path.

In yet another embodiment, the method 400 includes sterilizing the probe 351, 351' between uses or between use on different subjects. In one embodiment, for the probe 351, the tip 333 is sterilized by positioning the tip 333 in a sterilized solution for a fixed amount of time. In yet another embodiment, for the probe 351' with the replaceable caliper 360', the replaceable tip 333' is detached from the handle 356' and either disposed or sterilized using the same sterilization process as the tip 333.

2. Example Embodiments

Figure 6:
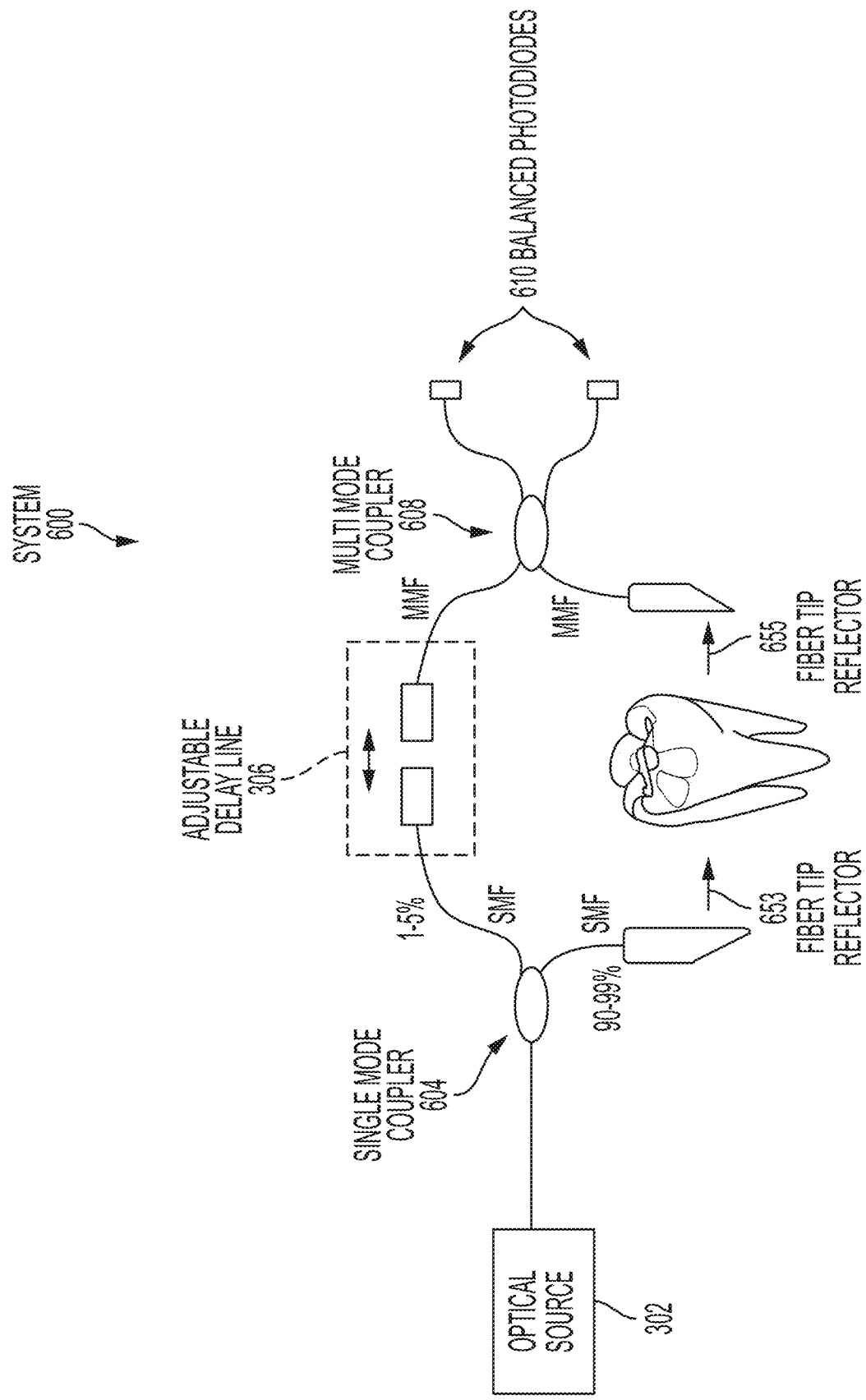
FIG. 6 is a block diagram that illustrates example components of a coherence gated Doppler (CGD) system for detecting tooth pulp vitality, according to various embodiments.

FIG. 6 is a block diagram that illustrates example components of a coherence gated Doppler (CGD) system 600 for detecting tooth pulp vitality, according to various embodiments. In an embodiment, the system 600 is similar to the system 300 with the exception of the features discussed herein. In an embodiment, a single mode (SM) coupler 604 is provided that receives output light from the optical source 302 and directs a first portion (e.g. 90-99%) into a single mode fiber (SMF) which couples the first portion of output light into the source line 352. The single mode coupler 604 also directs a second portion (e.g. 1-10%) into a SMF of the reference path and to the adjustable delay line 306. In an example embodiment, the single mode coupler 604 is a 2×1 single mode coupler.

In an embodiment, the source line 352 features a fiber tip reflector 653 at the tip 333a to direct the output light from the source line 352 into the tooth 551 at the predetermined angle (e.g. about 90 degrees) relative to the longitudinal axis 376. In another embodiment, the detector line 354 features a fiber tip reflector 655 at the tip 333b to receive the scattered light from the tooth 551 into the detector line 354.

In an embodiment, a multi mode coupler 608 is provided that receives output light from the adjustable delay line 306 through a multi mode fiber (MMF) and receives scattered light from the detector line 354 through a MMF. The multi mode coupler 608 directs the received output light and scattered light to a pair of balanced photodiodes 610 where the light from the reference path and scattered light from the detector line 354 generate an interference signal. One advantage of using the pair of balanced photodiodes 610 is a reduction of noise from the optical source 302 in generation of the interference signal. In an example embodiment, the multi mode (MM) coupler 608 is a 2×2 multi mode coupler.

Figure 7:
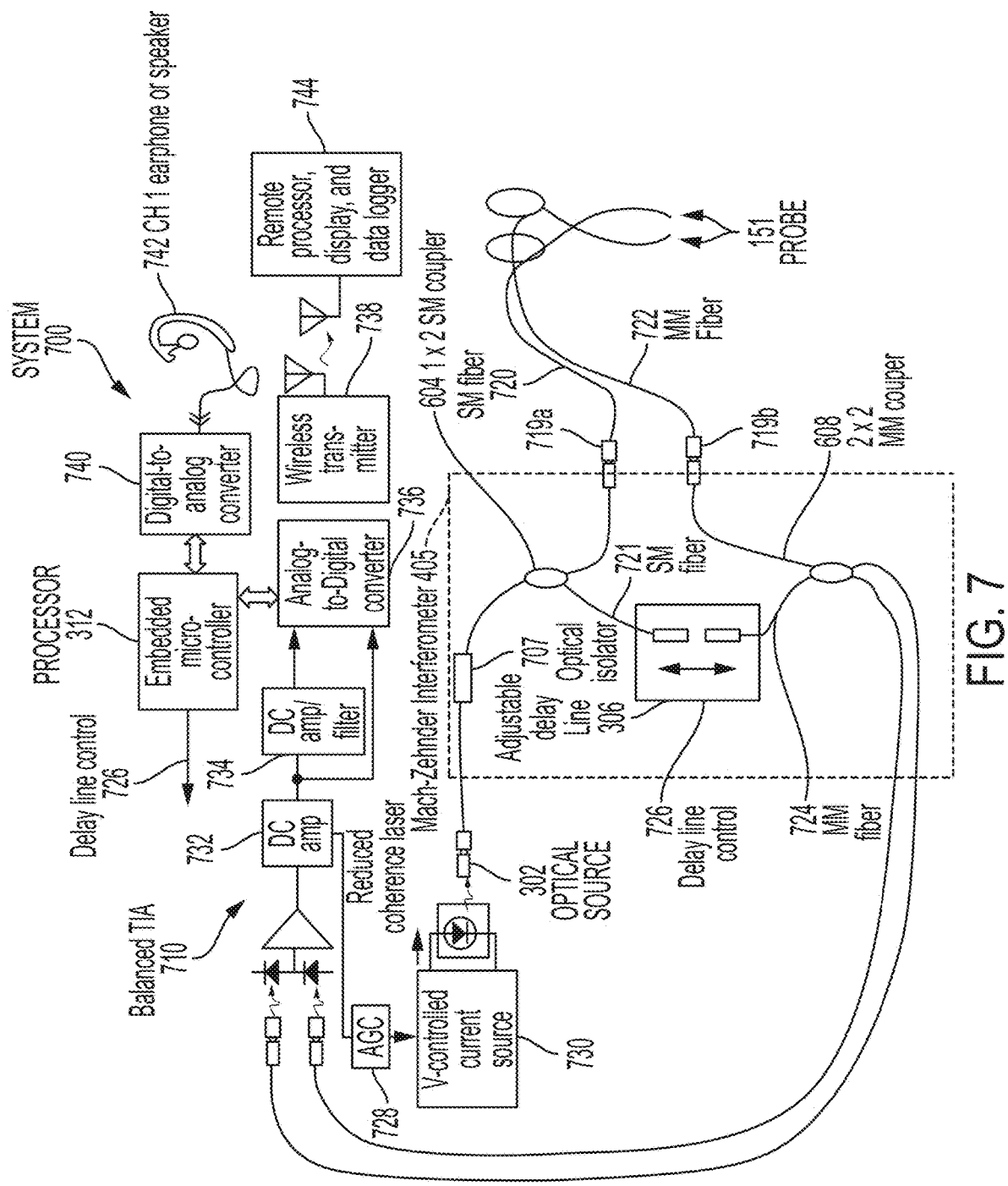
FIG. 7 is a block diagram that illustrates example components of a coherence gated Doppler (CGD) system for detecting tooth pulp vitality, according to various embodiments.

FIG. 7 is a block diagram that illustrates example components of a coherence gated Doppler (CGD) system 700 for detecting tooth pulp vitality, according to various embodiments. The system 700 is similar to the systems 300, 600 with the exception of the features discussed herein.

In step 402, the optical source 302 emits output light to a Mach-Zehnder Interferometer 405. In an embodiment, the output light enters the Mach-Zehnder Interferometer 405 and passes through an optical isolator 707 and to the Single Mode (SM) coupler 604. The first portion of output light (e.g. 90-99%) is directed from the SM coupler 604 and into a SM fiber 720 through a connector 719a. In an example embodiment, the connector 719a is a single mode to single mode connector. The first portion of output light is transmitted through the SM fiber 720 and into the source line 352 through the connector 353. In some embodiments, the SM fiber 720 should be long enough (e.g. 1-2 meters) to reach the connector 719a.

In an embodiment, the second portion of output light (e.g. 1-10%) is directed from the SM coupler 604 through a Single Mode (SM) fiber 721 and into the adjustable delay line 306. Light from the adjustable delay line 306 is directed into a Multi Mode (MM) fiber 724 and subsequently into the MM coupler 608. Additionally, scattered light from the detector line 354 is directed into a Multi Mode (MM) fiber 722 and into the MM coupler 608 through a connector 719b. In an example embodiment, the connector 719b is a Multi Mode to Multi Mode connector. In some embodiments, the MM fiber 722 should be long enough (e.g. 1-2 meters) to reach the connector 719b. The MM coupler 608 directs the output light from the adjustable delay line 306 and scattered light from the detector line 354 to the pair of balanced photodetectors 710 using a pair of MM fibers. In an embodiment, the MM fibers used in the system 700 are graded-index fibers with a 62.5 micron or 50 micron core. However, other fiber types known to practitioners of the art can be employed. One advantage of the MM fibers 722 that couple the detector line 354' to the MM coupler 608 and the MM fibers that direct the scattered light from the MM coupler 608 to the photodetectors 710 is that a large sample of scattered light is received from the pulp region 562 at the photodetectors 710 and thus the signal to noise ratio of scattered light from the pulp region 562 received at the photodetectors 710 exceeds a detection threshold.

In an example embodiment, the photodetectors 710 include a photodiode, an indium gallium arsenide (InGaAs) photodetector, a balanced detector, a charge-coupled device (CCD) and a Complementary metal-oxide-semiconductor (CMOS) photodetector. In some embodiments, a dual-balanced detection circuit is employed as a detector to improve signal-to-noise ratio by reducing common-mode noise.

In an embodiment, in step 404 light from the MM coupler 608 is received at the photodetectors 710 including output light from the reference path and scattered light from the detector line 354. The photodetectors 710 output an electronic signal, such as current or voltage, proportional to the electric or magnetic field that impinges the photodetectors 710. The signal output by the photodetectors 710 is passed to various components including a Direct Current (DC) amp 732, an Alternating Current (AC) amp 734 and/or an Analog to Digital Converter (ADC) 736 before a digital signal is transmitted to the processor 312. In an embodiment, the processor 312 analyzes the digital signal to determine whether to adjust the zero delay plane of the adjustable delay line 306. In step 406, if the processor 312 determines that the zero delay plane needs to be adjusted, a delay line control 726 signal is transmitted to the adjustable delay line 306 so that the zero delay plane is positioned in the pulp region 562. In one embodiment, in step 406 adjustable delay line 306 is adjusted automatically by the embedded processor 312 with the control signal 726 to maximize the interferometric signal strength generated by the pulp blood flow. In an example embodiment, either analog or digital signal processing, for example by the processor 312, is employed to emphasize the pulsatile component of the pulp flow for indication, including audio and/or visual indications.

In some of these embodiments, the optical interference signal at detectors 710 have high amplitude in frequencies between about 20 Hz and 20,000 Hz, and an analog output from the detectors 710 can directly drive an acoustic speaker 742 through a Digital to Analog converter 740 without the need for intervening significant processing or an intervening analog to digital converter (ADC). Acoustic output by the speakers 742 in this frequency range is audible to most humans. This enables the user to hear the difference in velocity as hand held probe tips 333a and 333b are moved across the tooth 551. Vessels associated with moving fluid can be associated with visual features determined while the user's eyes are trained on the tooth 551. This makes such embodiments suitable for real time guidance while keeping the system 700 light, simple and inexpensive, compared to both LDF and, especially, DOCT devices.

In some of these embodiments, a wireless transmitter 738 is provided to transmit the digital signal from the ADC 736 to a remote location where a remote processor or display 744 is located to process the signal in a manner similar to the processor 312. In some embodiments, the light source 302, such as a laser, and other electro-optical components, including an optical delay line 306, microcontroller 312, and a battery, of the optical tooth vitality testing system 700 are housed in a compact unit with wireless connectivity to a smart tablet or smart phone, for example, for separate processing and display 744. In other embodiments, the optical tooth vitality testing system 700 can be housed within a single portable instrument with wired connections among a pre-processor, processor, and display.

In an embodiment, in step 408 the processor 312 adjusts the bandwidth of the optical source 302 to vary the coherence length of the output light from the optical source 302. In one embodiment, the processor 312 transmits a signal through the DC amp 732 and Automatic Gain Control (AGC) 728 to a current source 730 to vary a current of the optical source 302 in order to adjust the bandwidth.

In one embodiment, a feedback loop adjusts the intensity of the light source 302 to accommodate a wide range of teeth with different attenuation characteristics. In one embodiment, in step 408 the processor 312 adjusts the current of the optical source 302 in response to an intensity of the scattered light received by the photodetectors 310 so that the intensity of the scattered light is adjusted to be above a threshold intensity. This advantageously accommodates a range of tooth thickness 502 that can affect the intensity of the scattered light received by the photodetectors 310 and correspondingly adjusts the intensity of the optical source 302 to ensure that a minimum threshold intensity of scattered light is received at the photodetectors 310 for a wide range of tooth thickness 502.

Most conventional semiconductor lasers do not have the properties required to achieve adequate sensitivity and selectivity to pulp blood flow. In an embodiment, the optical source 302 has one or more of the following characteristics: 1) a peak emission wavelength between about 1250 nm and about 1325 nm or between about 1600 nm and about 1700 nm; 2) an output power greater than about 5 mW; 3) a linewidth between about 0.25 mm and about 1 nm and having a single lobe emission profile (rather than, for example, a comb-like emission profile); 4) compact form; and 5) low cost of manufacture and operation.

In one embodiment, the optical source 302 includes a laser with custom-tailored coherence properties as light sources to satisfy. Mass-produced surface-mounted lasers, such as vertical-cavity surface-emitting lasers (VCSELs), emit low optical power (less than 2 mW) in a single mode and have the emission wavelength in a shorter wavelength band (approximately between 800 nm and 980 nm). Since the magnitude of the Doppler signal is proportional to source power and scattering losses in the tooth decrease with wavelength, short-wavelength VCSELs generally fall short of the ideal light sources for tooth vitality testing. In some embodiments, VCSELs can be manufactured to operate at longer wavelengths with appropriate linewidths and emission power levels. Other types of laser and light sources are contemplated, including integrated photonic circuits and lasers-on-a-chip, for example.

Although semiconductor Fabry-Perot (F-P) lasers are available with the desired power and peak wavelength characteristics, these lasers have a comb-like emission profile that produce multiple coherence time (or length) intervals. For example, a typical 1310 nm F-P laser has a narrow (e.g., less than 0.05 nm) main lobe and several equally narrow side lobes over a band of approximately between 1 nm and 2 nm, which generates a coherence function with multiple coherence intervals separated by approximately between 0.5 mm and 2 mm In one embodiment, the coherence function with such a comb-like shape produces an undesired sensitivity to optical paths longer than the coherence function from the main lobe alone. These side lobes can be suppressed, but the main lobe remains too narrow to restrict the coherence length to less than a few millimeters.

Figure 8:
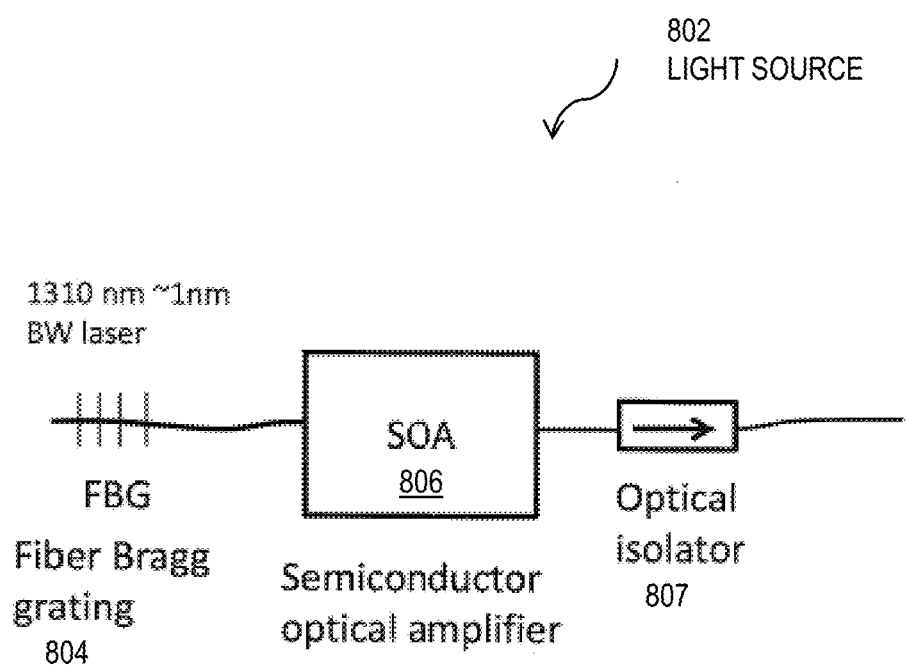
FIG. 8 is a block diagram that illustrates an example of a light source used in the system of FIG. 7, according to various embodiments.

FIG. 8 is a block diagram that illustrates an example of a light source 802 used in the system 700 of FIG. 7, according to various embodiments. In an embodiment, the light source 802 is capable of generating output light with the desired emission characteristics discussed above. In an embodiment, the light source 802 includes a Fiber Bragg Grating (FBG) 804, a Semiconductor Optical amplifier (SOA) 806 and an optical isolator 807. In an embodiment, an amplified spontaneous emission (ASE) from one terminal of the fiber-coupled SOA 806 is coupled into the custom reflective FBG 804. In an embodiment, the FBG 804 is configured to produce a smooth narrowband reflectance profile. Light is amplified by the SOA 806 in a single pass, is reflected by the FBG 804, and is emitted at the output terminal. The optical isolator 807 minimizes the effects of spurious reflections at the output terminal. In one embodiment, the light source 802 can generate a single emission line of light with a full-width-at-half-maximum (FWHM) width approximately between about 0.25 nm and about 1 nm at an output power greater than about 10 mW. In practice, the light source 802 is not absolutely single wavelength but comprises light in a very narrow wavelength band, typically with a wavelength bandwidth of about 0.08% of a center wavelength in the band or less.

FIG. 9A is a block diagram that illustrates an example of positioning a tip 333" of a probe 351" on opposite sides of a tooth 551 in the system of FIG. 7, according to various embodiments. In an embodiment, upon engagement of the tip 333" on the opposing surfaces of the tooth 551, an optical axis of the source line 352 in the tip 333" is roughly aligned with an optical axis of the detector line 354 in the tip 333". In some embodiments, anatomic constraints may not permit precise optical axis alignment of the source line 352 and detector line 354. In one example embodiment, it may be advantageous to direct the source line 352 and detector line 354 in the tip 333" slightly towards the apex of the root rather than directly towards each other.

In an embodiment, the tip 333" is covered with a soft clear material with high transmission of light in the visible to the mid-infrared spectrum (e.g. silicone). However, in other embodiments, the tip 333" excludes such soft clear material. In another embodiment, in step 401 the opposing sides of the tip 333" engage the tooth 551 at a cemento-enamel junction (CEJ) 951 of the tooth 551 so that output light is emitted from the tip 333" at or below the CEJ 951 and scattered light is received by the tip 333" at or below the CEJ 951. One advantage of engaging the tip 333" at or below the CEJ of the tooth is that dentine tissue below the CEJ and has better light transmitting properties than the calcified crown tissue that is above the CEJ. Another advantage of engaging the tip 333" at or below the CEJ is that an enamel layer, which is less transparent to the light is narrowed and/or absent below the CEJ 951. Thus, attaching the tip 333" at or below the CEJ 951 of the tooth 551 enhances the signal to noise ratio of scattered light from the pulp region 562 received at the detector 710. In yet another embodiment, in step 401 after the opposite sides of the tip 333" engage the CEJ of the tooth 551, the optical fibers 372a, 372b at the tip 333" can be adjusted relative to the tip 333" in order to optimize position of the fibers 372a, 372b relative to the surface of the tooth 551.

In one embodiment, the probe 351" depicted in FIG. 9A is smaller, lighter and simpler to build than the probe designs of FIGS. 3B and 3C. In one embodiment, the probe 351" is a disposable probe. In an embodiment, the fiber optic line 720 serving as the source line 352 is single mode. In one embodiment, the probe 351" is a single flexible unit with two caliper arms. In one example embodiment, the probe 351" has no handle or a much reduced handle as compared to the handles 356, 356' of the probes 351, 351'. In one example embodiment, the tip 333" is made from a spring like polymer. In another example embodiment, a spring is positioned adjacent the pivot of the probe 351". In an embodiment, the tip 333" has a soft clear low slippage material. In an embodiment, the two caliper arms containing the source line 352 and detector line 354 are surrounded and protected by a spring like polymer that allow the caliper arms to be opened and closed around the tooth 551. In some embodiments, the smaller probe 351" can be positioned and removed with a scissors like device that is used to open and close the calipers of the probe 351". In an example embodiment, the scissors like device opens or closes the caliper arms of the probe 351" by positioning each arm of the scissors like device between the tooth 551 and each caliper arm to press the caliper arms outward (open) or guide the caliper arms inward (close).

In one embodiment, in step 401 three contact points are established between the probe 351" and teeth of the subject to ensure that there is minimal movement during measurement. In one embodiment, a first contact point is established between a first side of the tip 333" and the tooth 551 for the delivery of the output light from the source line 352. A second contact point is established between the second side of the tip 333" and the tooth 551 for the detection of scattered light at the detector line 354. In an embodiment, the third contact is established to stabilize the probe tip 333" during engagement with the tooth 551. In some embodiments, the third contact point is a large surface rather than the small surface of the former two contact points. In one embodiment, the third contact point is on top of the crown and orthogonal to the axis of the tooth 551. In another embodiment, the third contact point is on neighboring teeth (e.g. crown of a neighboring tooth). In an embodiment, the first two contact points for engaging the tip 333" are positioned below the crown so that the forces from the three contact points oppose each other to effect mechanical stability. In an embodiment, the three contact points are covered with a stabilization contact 950 that is made from a thin non-rigid, clear, non-slip material to optimally hold the probe stationary on the tooth 551 and/or neighboring tooth.

Figure 9B:
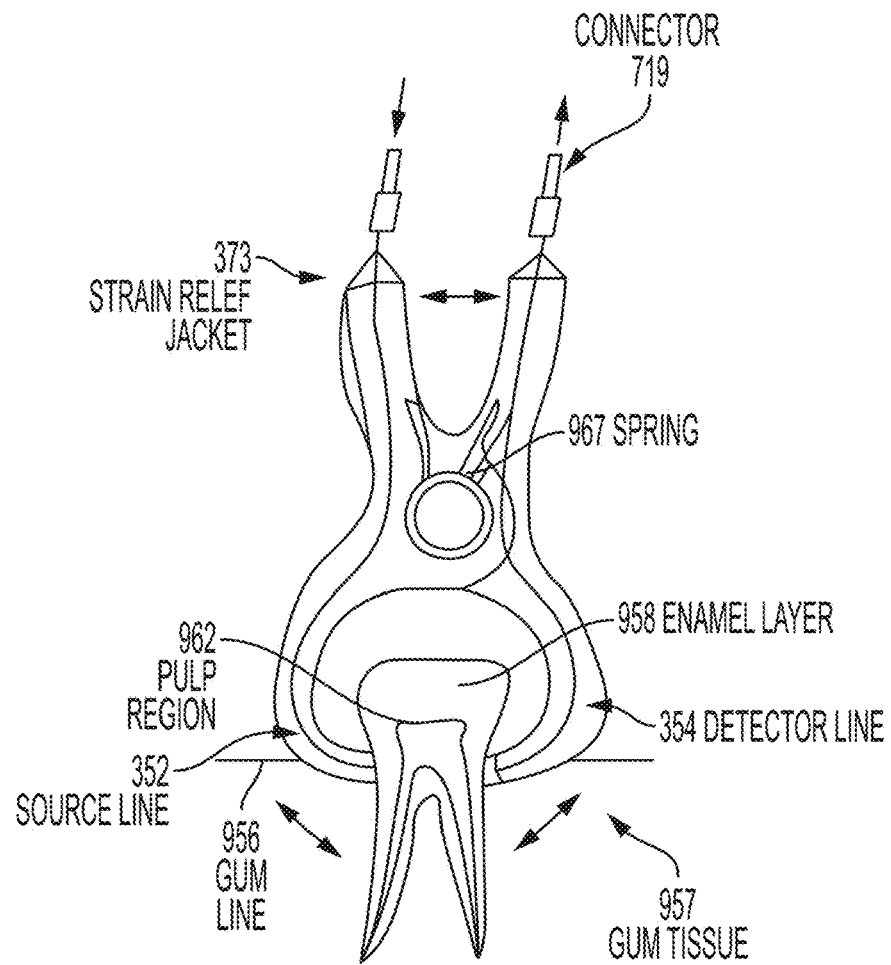
FIG. 9B is a block diagram that illustrates an example of positioning of a tip of the probe on opposite sides of a tooth below the gum line in the system of FIG. 7, according to various embodiments.

FIG. 9B is a block diagram that illustrates an example of positioning the tip 333 of the probe 351 on opposite sides of a tooth 551 below the gum line 956 in the system 700 of FIG. 7, according to various embodiments. In an embodiment, in step 401 the opposite sides of the tip 333 engages the gum line 956 and presses the gum tissue 957 adjacent the tooth 551 downward below the gum line 956. In an example embodiment in step 401 the opposite sides of the tip 333 presses the gum tissue 957 downward in order to access the CEJ 951 so that the tip 333 is positioned adjacent (e.g. at or below) to the CEJ 951. In an embodiment, in step 401 the opposite sides of the tip 333 engage the opposite sides of the tooth 551 below the gum line 956 after the gum tissue 957 adjacent the tooth 551 has been pressed down below the gum line 956. One advantage of this embodiment is that the tip 333, in addition to the source line 352 and detector line 354 are below an enamel layer 958 of the tooth 551 that is less transparent to output light from the optical source 302. Another advantage of this embodiment is that dentin which is more transparent to output light is between the tip 333 and the pulp region 962. In an example embodiment, in step 401 the tip 333 is positioned such that output light is emitted from the source line 352 and scattered light is received by the detector line 354 within about 0.5 mm of the gum tissue 957 after the gum tissue 957 has been pressed down by the tip 333. Thus, this arrangement advantageously enhances the signal to noise ratio of scattered light received from the pulp region 962.

In one embodiment, a spring 967 is positioned between opposite sides of the probe 351 in a vicinity of the pivot 358 to press opposing sides of the tip 333 together and thus maintain tip 333 engagement on opposing surfaces (e.g. buccal and lingual) of the tooth 551.

In an embodiment, the size and location of the pulp region 962 varies depending on the age of the subject. In one embodiment, for a younger subject the pulp region 962 extends well into the crown of the tooth 551. In another embodiment, for an older subject the pulp region 962 retracts downwards from the crown of the tooth 551.

In one embodiment, undesired scattered light along the optical path 570 (FIG. 5A) from the gum tissue 550 is scattered from periodontal ligament tissue that surrounds the root of the tooth 551. In yet another embodiment, the undesired scattered light is scattered from gingival tissue (e.g. gingival margin). The enamel layer 958 is highly calcified and strongly scatters the output light from the tip 333 whereas the dentine transmits the output light relatively well. In one embodiment, in step 401 the opposite sides of the tip 333 engage the tooth 551 at the cemento-enamel junction (where the enamel layer 958 has narrowed and merges with the cementum layer).

Access to the cemento-enamel junction varies based on the age and/or gum disease of the subject. In some embodiments, the probe is designed with different sizes or features, depending on the age or gum disease stage of the subject. In one example embodiment, access to the cemento-enamel junction is limited in young subjects. However, the pulp region 962 typically extends above the cemento-enamel junction and up into the crown of the tooth 551 in young subjects and the tooth 551 is less calcified. Accordingly, in one embodiment, in step 401 the opposite sides of the tip 333 engage the tooth 551 above the cemento-enamel junction and in the crown region of the tooth 551, for younger subjects. In another embodiment, in step 401 the opposite sides of the tip 333 engage the tooth 551 below the cemento-enamel junction for older subjects.

Figure 9C:
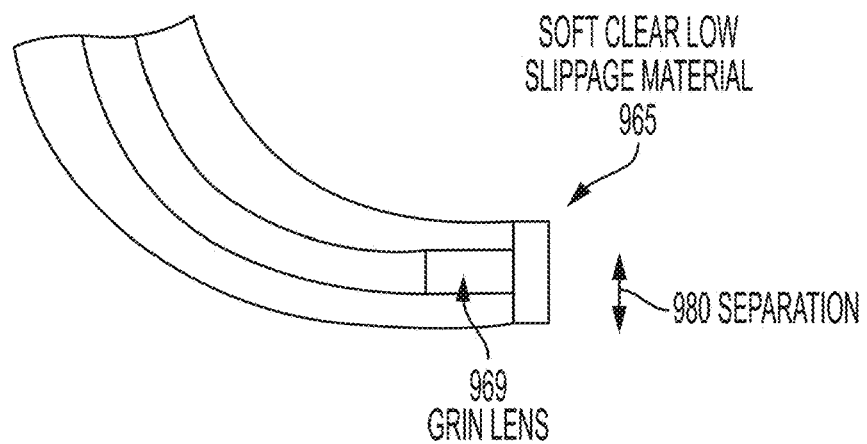
FIG. 9C is a block diagram that illustrates an example of a tip of the probe of FIG. 3A, according to various embodiments.

FIG. 9C is a block diagram that illustrates an example of a tip 333 of the probe 351 of FIG. 7, according to various embodiments. In an embodiment, the tip 333 includes the MMF fiber 372 of the source line 352 that terminate at a Gradient Index-Optics (GRIN) lens 969 and features a soft clear low slippage contact material 965. However, in some embodiments, the GRIN lens 969 is not used and is replaced with a different optical component. In another embodiment, the MMF fiber 372 terminates at a mirror that redirects output light from the source line 352 into the tooth 551 at the predetermined angle (e.g. about 90 degrees relative to the longitudinal axis 376). In yet another embodiment, the MMF fiber 372 is positioned within a separation 980 of an edge 335 of the tip 333 such that output light is emitted from the tip 333 at the separation 980 from the edge 335 of the tip 333. In an example embodiment, the separation 980 is equal to or less than a separation between the gum line 956 and the pulp region 962 (FIG. 9B). In an example embodiment, the optical fibers used in the source line 352 and/or detector line 354 are rated to transmit light with a radius of curvature in a range from about 5 mm to about 8 mm, which is sufficient for the curvature of the tip 333.

An advantage of the transmission mode of the probe tip 333 arrangement is that light is scattered stronger in a forward direction than compared to backscattering. Additionally, when a detector tip 333a and emitter tip 333b are in alignment, a spatial specificity can be improved for detecting signals from the target (e.g. pulp region 562) placed between the detector and emitter. Placing the emitter and detector on opposite sides of a target volume is generally not feasible for most medical applications but the probe tip 333 is advantageously configured to stably clip onto the tooth 551 for use in dentistry. Another challenge with using dental probes when imaging teeth is ensuring sterility of the probes between patients or uses. Thus, the probe tip 333' advantageously addresses this challenge by being detachable so that the tip 333' can be either disposed or sterilized between patients.

3. Hardware Overview

FIG. 10 is a block diagram that illustrates a computer system 1000 upon which an embodiment of the invention may be implemented. Computer system 1000 includes a communication mechanism such as a bus 1010 for passing information between other internal and external components of the computer system 1000. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1000, or a portion thereof, constitutes a means for performing one or more steps of one or more methods described herein.

A sequence of binary digits constitutes digital data that is used to represent a number or code for a character. A bus 1010 includes many parallel conductors of information so that information is transferred quickly among devices coupled to the bus 1010. One or more processors 1002 for processing information are coupled with the bus 1010. A processor 1002 performs a set of operations on information. The set of operations include bringing information in from the bus 1010 and placing information on the bus 1010. The set of operations also typically include comparing two or more units of information, shifting positions of units of information, and combining two or more units of information, such as by addition or multiplication. A sequence of operations to be executed by the processor 1002 constitutes computer instructions.

Computer system 1000 also includes a memory 1004 coupled to bus 1010. The memory 1004, such as a random access memory (RAM) or other dynamic storage device, stores information including computer instructions. Dynamic memory allows information stored therein to be changed by the computer system 1000. RAM allows a unit of information stored at a location called a memory address to be stored and retrieved independently of information at neighboring addresses. The memory 1004 is also used by the processor 1002 to store temporary values during execution of computer instructions. The computer system 1000 also includes a read only memory (ROM) 1006 or other static storage device coupled to the bus 1010 for storing static information, including instructions, that is not changed by the computer system 1000. Also coupled to bus 1010 is a non-volatile (persistent) storage device 1008, such as a magnetic disk or optical disk, for storing information, including instructions, that persists even when the computer system 1000 is turned off or otherwise loses power.

Information, including instructions, is provided to the bus 1010 for use by the processor from an external input device 1012, such as a keyboard containing alphanumeric keys operated by a human user, or a sensor. A sensor detects conditions in its vicinity and transforms those detections into signals compatible with the signals used to represent information in computer system 1000. Other external devices coupled to bus 1010, used primarily for interacting with humans, include a display device 1014, such as a cathode ray tube (CRT) or a liquid crystal display (LCD), for presenting images, and a pointing device 1016, such as a mouse or a trackball or cursor direction keys, for controlling a position of a small cursor image presented on the display 1014 and issuing commands associated with graphical elements presented on the display 1014.

In the illustrated embodiment, special purpose hardware, such as an application specific integrated circuit (IC) 1020, is coupled to bus 1010. The special purpose hardware is configured to perform operations not performed by processor 1002 quickly enough for special purposes. Examples of application specific ICs include graphics accelerator cards for generating images for display 1014, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1000 also includes one or more instances of a communications interface 1070 coupled to bus 1010. Communication interface 1070 provides a two-way communication coupling to a variety of external devices that operate with their own processors, such as printers, scanners and external disks. In general the coupling is with a network link 1078 that is connected to a local network 1080 to which a variety of external devices with their own processors are connected. For example, communication interface 1070 may be a parallel port or a serial port or a universal serial bus (USB) port on a personal computer. In some embodiments, communications interface 1070 is an integrated services digital network (ISDN) card or a digital subscriber line (DSL) card or a telephone modem that provides an information communication connection to a corresponding type of telephone line. In some embodiments, a communication interface 1070 is a cable modem that converts signals on bus 1010 into signals for a communication connection over a coaxial cable or into optical signals for a communication connection over a fiber optic cable. As another example, communications interface 1070 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1070 sends and receives electrical, acoustic or electromagnetic signals, including infrared and optical signals, that carry information streams, such as digital data.

The term computer-readable medium is used herein to refer to any medium that participates in providing information to processor 1002, including instructions for execution. Such a medium may take many forms, including, but not limited to, non-volatile media, volatile media and transmission media. Non-volatile media include, for example, optical or magnetic disks, such as storage device 1008. Volatile media include, for example, dynamic memory 1004. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1002, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1002, except for carrier waves and other signals.

Logic encoded in one or more tangible media includes one or both of processor instructions on a computer-readable storage media and special purpose hardware, such as ASIC *1020.

Network link 1078 typically provides information communication through one or more networks to other devices that use or process the information. For example, network link 1078 may provide a connection through local network 1080 to a host computer 1082 or to equipment 1084 operated by an Internet Service Provider (ISP). ISP equipment 1084 in turn provides data communication services through the public, world-wide packet-switching communication network of networks now commonly referred to as the Internet 1090. A computer called a server 1092 connected to the Internet provides a service in response to information received over the Internet. For example, server 1092 provides information representing video data for presentation at display 1014.

The invention is related to the use of computer system 1000 for implementing the techniques described herein. According to one embodiment of the invention, those techniques are performed by computer system 1000 in response to processor 1002 executing one or more sequences of one or more instructions contained in memory 1004. Such instructions, also called software and program code, may be read into memory 1004 from another computer-readable medium such as storage device 1008. Execution of the sequences of instructions contained in memory 1004 causes processor 1002 to perform the method steps described herein. In alternative embodiments, hardware, such as application specific integrated circuit 1020, may be used in place of or in combination with software to implement the invention. Thus, embodiments of the invention are not limited to any specific combination of hardware and software.

The signals transmitted over network link 1078 and other networks through communications interface 1070, carry information to and from computer system 1000. Computer system 1000 can send and receive information, including program code, through the networks 1080, 1090 among others, through network link 1078 and communications interface 1070. In an example using the Internet 1090, a server 1092 transmits program code for a particular application, requested by a message sent from computer 1000, through Internet 1090, ISP equipment 1084, local network 1080 and communications interface 1070. The received code may be executed by processor 1002 as it is received, or may be stored in storage device 1008 or other non-volatile storage for later execution, or both. In this manner, computer system 1000 may obtain application program code in the form of a signal on a carrier wave.

Various forms of computer readable media may be involved in carrying one or more sequence of instructions or data or both to processor 1002 for execution. For example, instructions and data may initially be carried on a magnetic disk of a remote computer such as host 1082. The remote computer loads the instructions and data into its dynamic memory and sends the instructions and data over a telephone line using a modem. A modem local to the computer system 1000 receives the instructions and data on a telephone line and uses an infra-red transmitter to convert the instructions and data to a signal on an infra-red a carrier wave serving as the network link 1078. An infrared detector serving as communications interface 1070 receives the instructions and data carried in the infrared signal and places information representing the instructions and data onto bus 1010. Bus 1010 carries the information to memory 1004 from which processor 1002 retrieves and executes the instructions using some of the data sent with the instructions. The instructions and data received in memory 1004 may optionally be stored on storage device 1008, either before or after execution by the processor 1002.

FIG. 11 illustrates a chip set 1100 upon which an embodiment of the invention may be implemented. Chip set 1100 is programmed to perform one or more steps of a method described herein and includes, for instance, the processor and memory components described with respect to FIG. *10 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1100, or a portion thereof, constitutes a means for performing one or more steps of a method described herein.

In one embodiment, the chip set 1100 includes a communication mechanism such as a bus 1101 for passing information among the components of the chip set 1100. A processor 1103 has connectivity to the bus 1101 to execute instructions and process information stored in, for example, a memory 1105. The processor 1103 may include one or more processing cores with each core configured to perform independently. A multi-core processor enables multiprocessing within a single physical package. Examples of a multi-core processor include two, four, eight, or greater numbers of processing cores. Alternatively or in addition, the processor 1103 may include one or more microprocessors configured in tandem via the bus 1101 to enable independent execution of instructions, pipelining, and multithreading. The processor 1103 may also be accompanied with one or more specialized components to perform certain processing functions and tasks such as one or more digital signal processors (DSP) 1107, or one or more application-specific integrated circuits (ASIC) 1109. A DSP 1107 typically is configured to process real-world signals (e.g., sound) in real time independently of the processor 1103. Similarly, an ASIC 1109 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1103 and accompanying components have connectivity to the memory 1105 via the bus 1101. The memory 1105 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1105 also stores the data associated with or generated by the execution of one or more steps of the methods described herein.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

4. References

A. Ahmad, S G. Adie, M Wang, and S A. Boppart, "Sonification of optical coherence tomography data and images," *Opt. Express* v18, pp9934-9944 (2010).

C. Andrews, I. Aviles-Olmos, M. Hariz, and T. Foltynie, "Which patients with dystonia benefit from deep brain stimulation? A metaregression of individual patient outcomes," *Journal of Neurology Neurosurgery and Psychiatry* v81, pp1383-1389 (2010).

D. K. Binder, G. M. Rau, and P. A. Starr, "Hemorrhagic complications of microelectrode-guided deep brain stimulation," *Stereotactic and Functional Neurosurgery* v80, pp28-31 (2003).

D. K. Binder, G. M. Rau, and P. A. Starr, "Risk factors for hemorrhage during microelectrode-guided deep brain stimulator implantation for movement disorders," *Neurosurgery* v56, pp22-'732; discussion pp722-732 (2005).

J. M. Bronstein, M. Tagliati, R. L. Alterman, A. M. Lozano, J. Volkmann, A. Stefani, F. B. Horak, M. S. Okun, K. D. Foote, P. Krack, R. Pahwa, J. M. Henderson, M. I. Hariz, R. A. Bakay, A. Rezai, W. J. Marks, Jr., E. Moro, J. L. Vitek, F. M. Weaver, R. E. Gross, and M. R. DeLong, "Deep brain stimulation for Parkinson disease: an expert consensus and review of key issues," *Archives of Neurology* v68, p165 (2010).

D. J. Caplan, J. B. Chasen, E. A. Krall, J. Cai, S. Kang, R. I. Garcia, S. Offenbacher, J. D. Beck, "Lesions of endodontic origin and risk of coronary heart disease," *Journal of Dental Research* v85 n11, pp996-1000 (2006).

Z. P. Chen, T. E. Milner, S. Srinivas, X. J. Wang, A. Malekafzali, M. J. C. vanGemert, and J. S. Nelson, "Noninvasive imaging of in vivo blood flow velocity using optical Doppler tomography," *Optics Letters* v22, pp1119-1121 (1997).

G. Deuschl, J. Herzog, G. Kleiner-Fisman, C. Kubu, A. M. Lozano, K. E. Lyons, M. C. Rodriguez-Oroz, F. Tamma, A. I. Troster, J. L. Vitek, J. Volkmann, and V. Voon, "Deep brain stimulation: Postoperative issues," *Movement Disorders* v21, ppS219-S237 (2006).

H. C. Eun, "Evaluation of skin blood flow by laser Doppler flowmetry," *Clin Dermatol* v13, pp337-347 (1995).

E. D. Flora, C. L. Perera, A. L. Cameron, and G. J. Maddern, "Deep Brain Stimulation for Essential Tremor: A Systematic Review," *Movement Disorders* v25, pp1550-1559 (2010).

I. Fredriksson, C. Fors, and J. Johansson, "Laser Doppler Flowmetry—A Theoretical Framework," Department of Biomedical Engineering, Linköping University (2007).

B. Gazelius, L. Olgart, and B. Edwall, "Restored vitality in luxated teeth assessed by laser Doppler flowmeter," *Endodontics & Dental Traumatology* v4, pp265-268 (1988).

A. Gorgulho, A. A. De Salles, L. Frighetto, and E. Behnke, "Incidence of hemorrhage associated with electrophysiological studies performed using macroelectrodes and microelectrodes in functional neurosurgery," *Journal of Neurosurgery* v102, pp888-896 (2005).

M. I. Hariz, "Complications of deep brain stimulation surgery," *Movement Disorders* v17, ppS162-S166 (2002).

R. S. Jones, G. D. Huynh, G. C. Jones, and D. Fried, "Near-infrared transillumination at 1310-nm for the imaging of early dental decay," *Optics Express* v11, pp2259-2265 (2003).

K. Kijsamanmith, S. Timpawat, N. Vongsavan, and B. Matthews, "Pulpal blood flow recorded from human premolar teeth with a laser Doppler flow meter using either red or infrared light," *Arch Oral Biol* v56, pp629-633 (2011).

P. N. Kongkham, E. Knifed, M. S. Tamber, and M. Bernstein, "Complications in 622 cases of frame-based stereotactic biopsy, a decreasing procedure," *Canadian Journal of Neurological Sciences* v35, pp79-84 (2008).

A. V. Kulkarni, A. Guha, A. Lozano, and M. Bernstein, "Incidence of silent hemorrhage and delayed deterioration after stereotactic brain biopsy," *Journal of Neurosurgery* v89, pp31-35 (1998).

P. Mohr, "Deep Brain Stimulation in Psychiatry," Neuroendocrinology Letters v29, pp123-132 (2008). M. Nishihara, T. Sasayama, H. Kudo, and E. Kohmura, "Morbidity of stereotactic biopsy for intracranial lesions," *Kobe Journal of Medical Sciences* v56, ppE148-153 (2010).

W. C. Noblett, L. R. Wilcox, F. Scamman, W. T. Johnson, and A. Diaz-Arnold, "Detection of pulpal circulation in vitro by pulse oximetry," *Journal of Endodontics* v22, pp1-5 (1996).

L. Olgart, B. Gazelius, and U. Lindh-Stromberg, "Laser Doppler flowmetry in assessing vitality in luxated permanent teeth," *International Endodontic Journal* v21, pp300-306 (1988).

K. Petersson, C. Soderstrom, M. Kiani-Anaraki, and G. Levy, "Evaluation of the ability of thermal and electrical tests to register pulp vitality," *Endodontics & Dental Traumatology* v15, pp127-131 (1999).

G. Podoleanu, "Unbalanced versus balanced operation in an optical coherence tomography system," *Applied Optics* v39, pp173-182 (2000).

M. H. Pozzobon, R. de Sousa Vieira, A. M. Alves, J. Reyes-Carmona, C. S. Teixeira, B. D. de Souza, and W. T. Felippe, "Assessment of pulp blood flow in primary and permanent teeth using pulse oximetry," *Dental Traumatology* v27, pp184-188 (2011).

C. A. Sansur, R. C. Frysinger, N. Pouratian, K. M. Fu, M. Bittl, R. J. Oskouian, E. R. Laws, and W. J. Elias, "Incidence of symptomatic hemorrhage after stereotactic electrode placement," *Journal of Neurosurgery* v107, pp998-1003 (2007).

J. M. Schmitt, R. L. Webber, and E. C. Walker, "Optical determination of dental pulp vitality," *IEEE Transactions on Biomedical Engineering* v38, pp346-352 (1991).

F. M. Skidmore, R. L. Rodriguez, H. H. Fernandez, W. K. Goodman, K. D. Foote, and M. S. Okun, "Lessons learned in deep brain stimulation for movement and neuropsychiatric disorders," *CNS Spectrums* v11, pp521+(2006).

S. Soo-ampon, N. Vongsavan, M. Soo-ampon, S. Chuckpaiwong, and B. Matthews, "The sources of laser Doppler blood-flow signals recorded from human teeth," *Archives of Oral Biology* v48, pp353-360 (2003).

T. Terao, H. Takahashi, F. Yokochi, M. Taniguchi, R. Okiyama, and I. Hamada, "Hemorrhagic complication of stereotactic surgery in patients with movement disorders," *Journal of Neurosurgery* v98, pp1241-1246 (2003).

B. Varghese, V. Rajan, T. G. Van Leeuwen, and W. Steenbergen, "Path-length-resolved measurements of multiple scattered photons in static and dynamic turbid media using phasemodulated low-coherence interferometry," *Journal of Biomedical Optics* v12 (2007).

J. Voges, R. Hilker, K. Botzel, K. L. Kiening, M. Moss, A. Kupsch, A. Schnitzler, G. H. Schneider, U. Steude, G. Deuschl, and M. O. Pinsker, "Thirty days complication rate following surgery performed for deep-brain-stimulation," *Movement Disorders* v22, pp1486-1489 (2007).

K. Wardell, P. Blomstedt, J. Richter, J. Antonsson, O. Eriksson, P. Zsigmond, A. T. Bergenheim, and M. I. Hariz, "Intracerebral microvascular measurements during deep brain stimulation implantation using laser Doppler perfusion monitoring," *Stereotactic and Functional Neurosurgery* v85, pp279-286 (2007).

R. Weisleder, S. Yamauchi, D. J. Caplan, M. Trope, and F. B. Teixeira, "The validity of pulp testing: a clinical study," *Journal of the American Dental Association* v140, pp1013-1017 (2009).

V. X. D. Yang, M. L. Gordon, B. Qi, J. Pekar, S. Lo, E. Seng-Yue, A. Mok, B. C. Wilson, and I. A. Vitkin, "High speed, wide velocity dynamic range Doppler optical coherence tomography (Part I): System design, signal processing, and performance," *Opt Express* v11, pp794-809 (2003).

What is claimed is:

1. An apparatus comprising:
a handle;
a pivot;
a caliper; and
a pair of fiber optic lines passing through an interior of the handle, the pivot and the caliper;
wherein one of the fiber optic lines is a source line with a connector at an end of the source line and wherein the source line is single mode in the handle;
wherein another of the fiber optic lines is a detector line with a connector at an end of the detector line and wherein the detector line is multi mode;
wherein the caliper includes a tip configured to engage opposite sides of a sample;
wherein the source line is configured to receive light from an optical source having a coherence length; and
wherein the tip is configured such that a difference between a first optical path along the source line and the detector line through a target volume of the sample and a second optical path along the source line and the detector line through a non-target volume of the sample exceeds the coherence length of the light to optically suppress signals from the non-target volume at the detector line such that the signals from the non-target volume do not interfere at the detector line and such that motion within the target volume is measured while motion within the non-target volume is suppressed.

2. An apparatus as recited in claim 1, wherein the caliper is removable and wherein the source line is multi mode in the caliper.

3. An apparatus as recited in claim 2, wherein the source line includes a single mode to multi mode connector between the handle and the caliper and wherein the detector line includes a multi mode to multi mode connector between the handle and the caliper.

4. An apparatus as recited in claim 1, wherein a thickness of the tip of the caliper is sized such that the light from the source line is configured to be emitted from the tip within about 0.5 mm of an edge of the tip.

5. An apparatus as recited in claim 1, wherein the tip of the caliper is configured such that the light from the source line is emitted from the tip at an angle of about 90 degrees relative to a longitudinal axis of the tip.

6. An apparatus as recited in claim 5, wherein an interior of the caliper includes an angled surface at the tip that is configured to reflect the light at the angle.

7. An apparatus as recited in claim 6, wherein the angled surface is oriented at about 45 degrees relative to the longitudinal axis of the tip.

8. An apparatus as recited in claim 6, wherein the angled surface is configured to reflect the light at the angle using total internal reflection within the tip of the caliper.

9. An apparatus as recited in claim 1, wherein an end of the source line comprises a polished angled surface that is oriented at about 45 degrees relative to a longitudinal axis of the tip such that the light from the source line is emitted from the tip at an angle of about 90 degrees relative to the longitudinal axis of the tip.

10. An apparatus as recited in claim 1, wherein the handle and the caliper are integral.

11. An apparatus as recited in claim 1, wherein the first optical path includes:
a first diffusion length where the light incident from the source line propagates in a straight direction within the sample;

a path where the light deviates and is scattered from the target-volume of the sample; and a second diffusion length where the scattered light from the target-volume propagates in a straight direction before exiting the sample and into the detector line.

12. An apparatus as recited in claim 11, wherein the second optical path includes:

a diffusion length where the light incident from the source line propagates in a straight direction within the sample;

a path where the light backscatters to the non-target volume;

a path where the light scatters from the non-target volume and enters the detector line.

13. The apparatus as recited in claim 1, wherein the sample is a tooth, the non-target volume is gum tissue and the target volume is a pulp region.

14. An apparatus comprising:

a probe;

a pair of fiber optic lines passing through an interior of the probe;

wherein one of the fiber optic lines is a source line with a connector at an end of the source line;

wherein another of the fiber optic lines is a detector line with a connector at an end of the detector line;

wherein the probe includes a tip configured to engage opposite sides of a sample;

wherein the source line is configured to receive light from an optical source having a coherence length; and wherein the tip is configured such that a difference between a first optical path along the source line and the detector line through a target volume of the sample and a second optical path along the source line and the detector line through a non-target volume of the sample exceeds the coherence length of the light to optically suppress signals from the non-target volume at the detector line such that the signals from the non-target volume do not interfere at the detector line and such that motion within the target volume is measured while motion within the non-target volume is suppressed.

15. The apparatus as recited in claim 14, wherein the probe comprises:

a handle;

a pivot; and a caliper including the tip.

16. The apparatus as recited in claim 15, wherein the pair of optical fibers pass through an interior of the handle, the pivot and the caliper.

17. The apparatus as recited in claim 14, wherein the source line is single mode and the detector line is multi mode.

18. The apparatus as recited in claim 14, wherein the probe is a tooth probe such that the tip is configured to engage opposite sides of a tooth of the sample, wherein the target volume is a pulp region within the tooth and wherein the scattered light from outside the target volume includes scattered light from gum tissue of the sample.

19. The apparatus as recited in claim 18, wherein the tip is further configured to push aside a gum tissue at a base of the tooth to access a cemento-enamel junction (CEJ) of the tooth.

20. The apparatus as recited in claim 18, wherein the coherence length of the light is in a range from about 2 mm to about 4 mm.

* * * * *